(12) United States Patent
Bourque et al.

(10) Patent No.: US 12,075,998 B2
(45) Date of Patent: Sep. 3, 2024

(54) TISSUE REPAIR DEVICE

(71) Applicant: Smith & Nephew, Inc., Memphis, TN (US)

(72) Inventors: Bernard J. Bourque, Taunton, MA (US); William R. Davis, Hingham, MA (US); Scott Freedman, Chicago, IL (US)

(73) Assignee: Smith & Nephew, Inc., Memphis, TN (US)

(*) Notice: Subject to any disclaimer, the term of this patent is extended or adjusted under 35 U.S.C. 154(b) by 434 days.

(21) Appl. No.: 17/483,887

(22) Filed: Sep. 24, 2021

(65) Prior Publication Data

US 2022/0008062 A1 Jan. 13, 2022

Related U.S. Application Data

(63) Continuation of application No. 16/506,181, filed on Jul. 9, 2019, now Pat. No. 11,179,148, which is a
(Continued)

(51) Int. Cl.
*A61B 17/04* (2006.01)
*A61B 17/06* (2006.01)
*A61B 17/29* (2006.01)

(52) U.S. Cl.
CPC ...... *A61B 17/0401* (2013.01); *A61B 17/0469* (2013.01); *A61B 17/0482* (2013.01);
(Continued)

(58) Field of Classification Search
CPC ............ A61B 17/0401; A61B 17/0469; A61B 17/0482; A61B 17/0483; A61B 17/2909;
(Continued)

(56) References Cited

U.S. PATENT DOCUMENTS

| 312,199 A | * | 2/1885 | Ginter | B25C 1/003 |
| | | | | 227/147 |
| 3,656,520 A | * | 4/1972 | Caffa | B25B 23/045 |
| | | | | 81/433 |

(Continued)

FOREIGN PATENT DOCUMENTS

| CN | 1128217 A | 8/1996 |
| CN | 1761429 A | 4/2006 |

(Continued)

*Primary Examiner* — Robert A Lynch
(74) *Attorney, Agent, or Firm* — ArentFox Schiff LLP; Joseph M. Maraia; Marlo Schepper Grolnic

(57) ABSTRACT

The present disclosure relates to a tissue repair device. The device includes a handle, a knob coupled to the handle, and a needle coupled to the handle. The needle includes a proximal end and a distal end, the distal end including a slot, wherein a first anchor is housed within the distal end and a second anchor is housed within the slot and located proximal to the first anchor. An actuator disposed within the needle and operatively coupled to the knob, wherein advancement of the knob allows for engagement of the actuator with the first anchor and subsequent advancement of the first anchor via the actuator. A method of tissue repair is also disclosed.

20 Claims, 44 Drawing Sheets

Related U.S. Application Data continuation of application No. 15/391,287, filed on Dec. 27, 2016, now Pat. No. 10,390,815, which is a continuation of application No. 14/242,171, filed on Apr. 1, 2014, now Pat. No. 9,549,725, which is a continuation of application No. 12/623,930, filed on Nov. 23, 2009, now Pat. No. 8,888,798.

(60) Provisional application No. 61/255,995, filed on Oct. 29, 2009, provisional application No. 61/166,907, filed on Apr. 6, 2009, provisional application No. 61/117,987, filed on Nov. 26, 2008.

(52) U.S. Cl.
CPC .. *A61B 17/0483* (2013.01); *A61B 2017/0409* (2013.01); *A61B 2017/0417* (2013.01); *A61B 2017/0419* (2013.01); *A61B 2017/0475* (2013.01); *A61B 2017/06052* (2013.01); *A61B 17/2909* (2013.01)

(58) Field of Classification Search
CPC .... A61B 2017/0409; A61B 2017/0417; A61B 2017/0419; A61B 2017/0475; A61B 2017/06052

See application file for complete search history.

(56) References Cited

U.S. PATENT DOCUMENTS

| | | | |
|---|---|---|---|
| 4,936,169 A * | 6/1990 | Parsons | F16B 27/00 |
| | | | 81/177.4 |
| 5,713,680 A | 2/1998 | Yoshino et al. | |
| 7,461,574 B2 * | 12/2008 | Lewis | A61B 17/862 |
| | | | 606/104 |
| 7,771,429 B2 * | 8/2010 | Ballard | A61B 17/8875 |
| | | | 606/86 R |
| 10,390,815 B2 | 8/2019 | Bourque et al. | |
| 2004/0002734 A1 | 1/2004 | Fallin et al. | |
| 2005/0033363 A1 * | 2/2005 | Bojarski | A61B 17/06166 |
| | | | 606/228 |
| 2005/0251208 A1 | 11/2005 | Elmer et al. | |

FOREIGN PATENT DOCUMENTS

| | | |
|---|---|---|
| CN | 102292032 A | 12/2011 |
| WO | 2008021691 A2 | 2/2008 |

\* cited by examiner

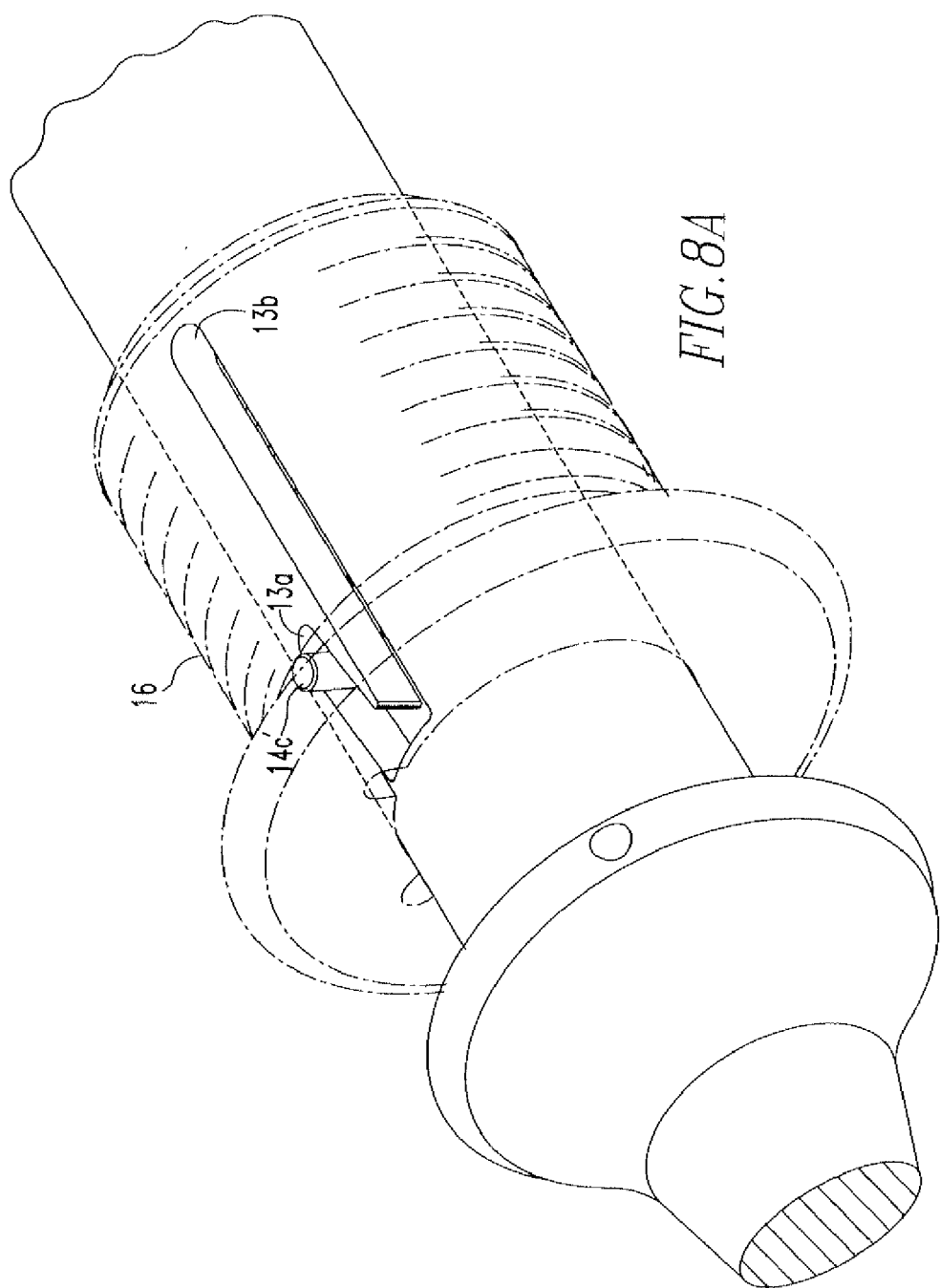

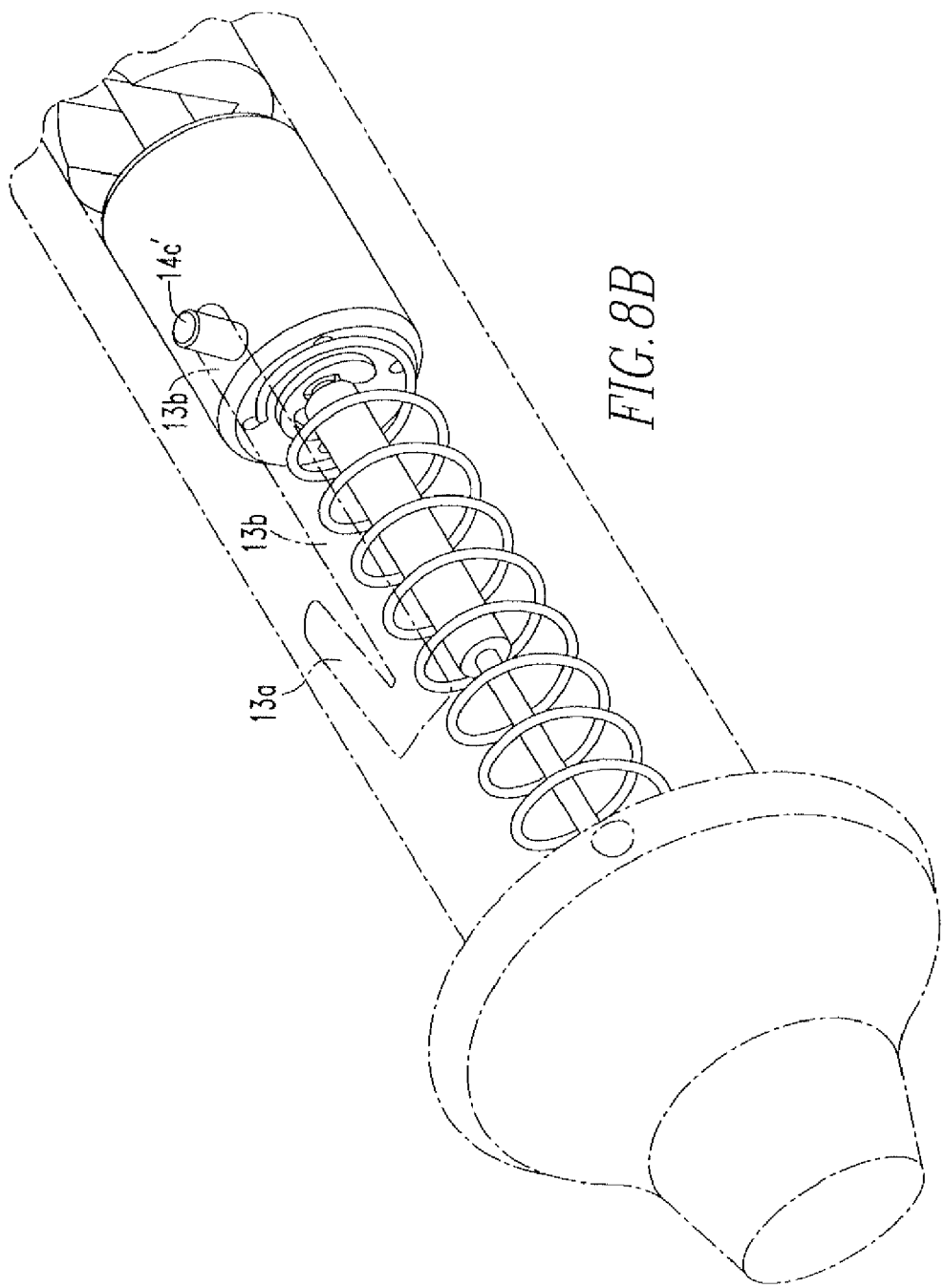

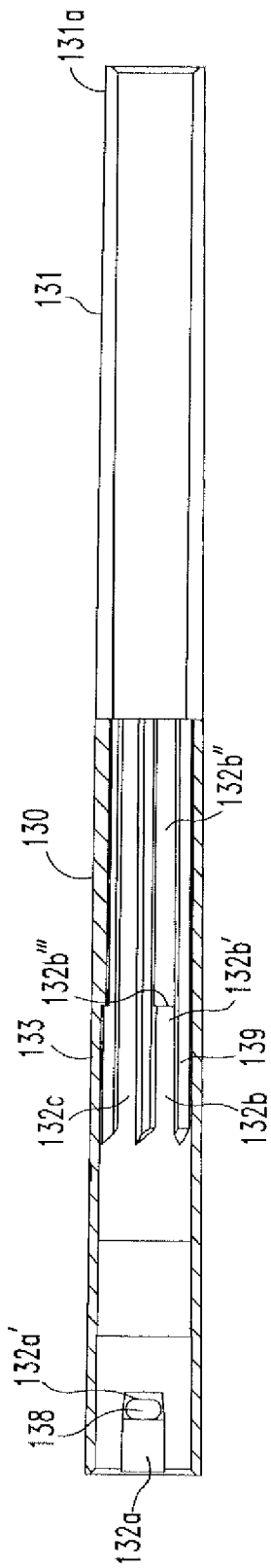

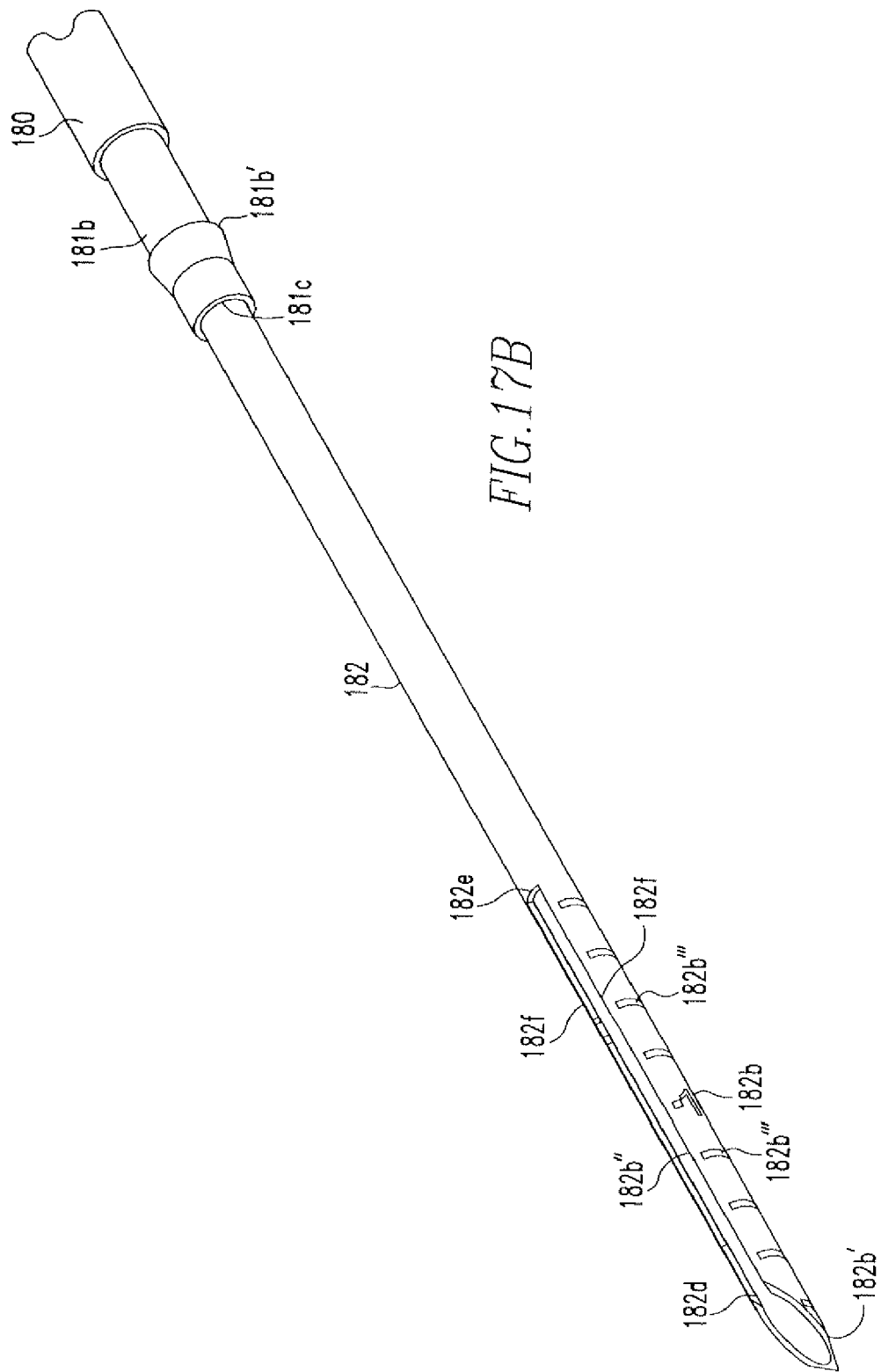

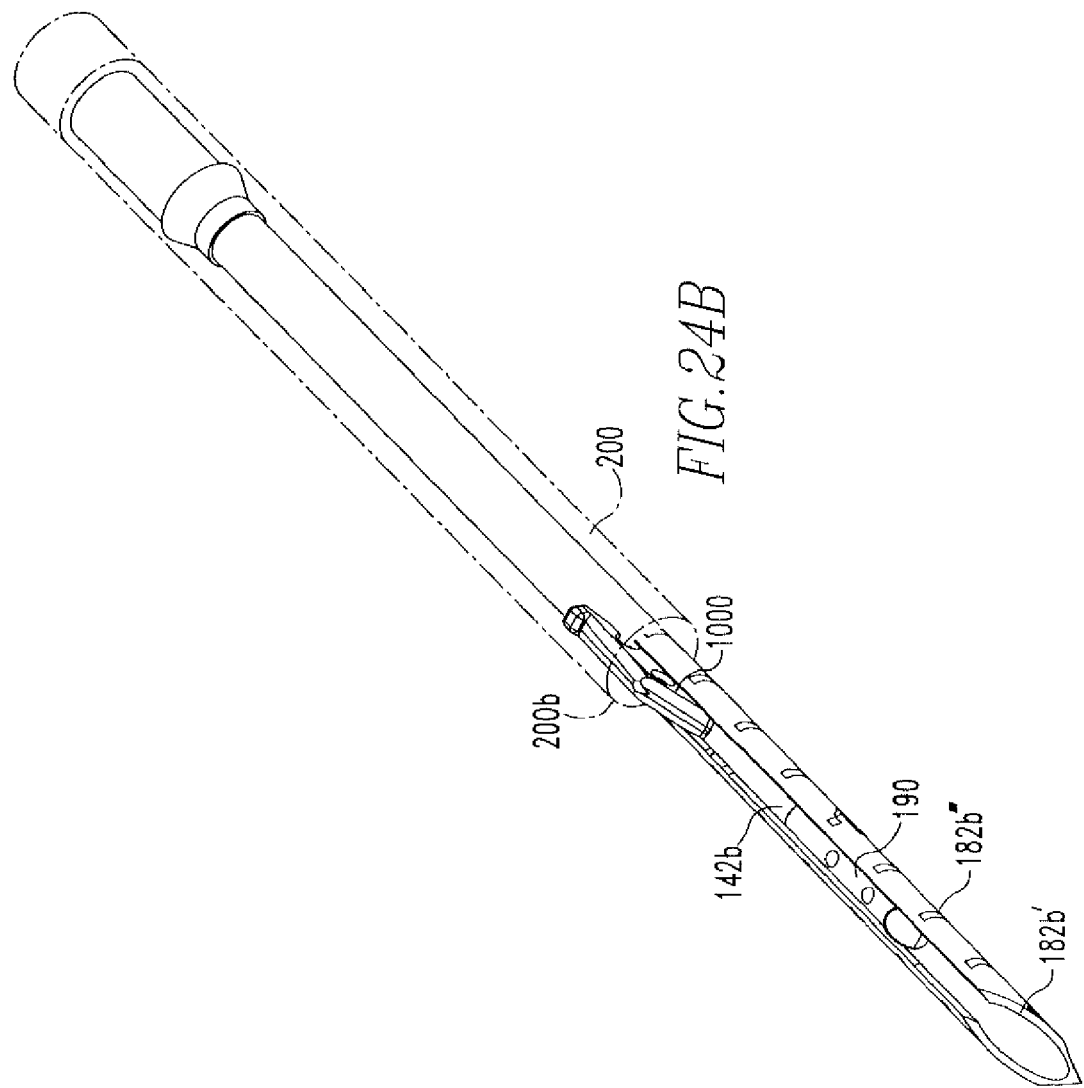

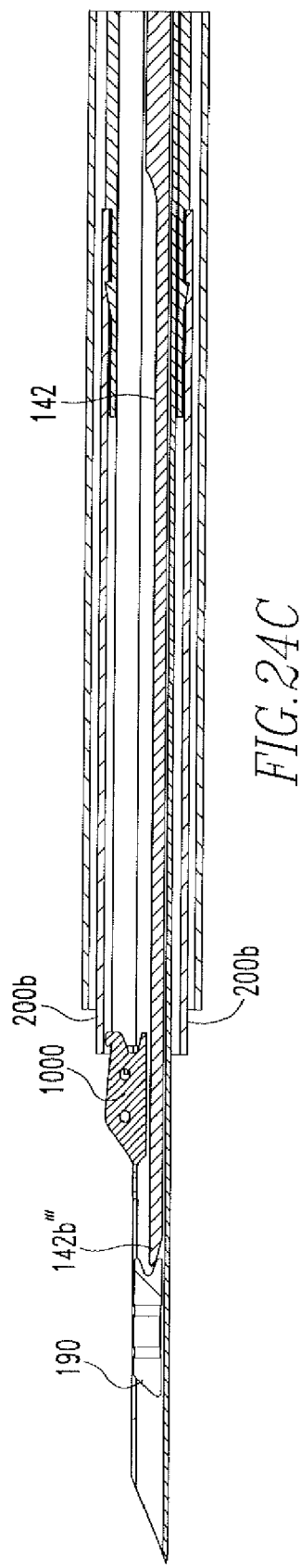

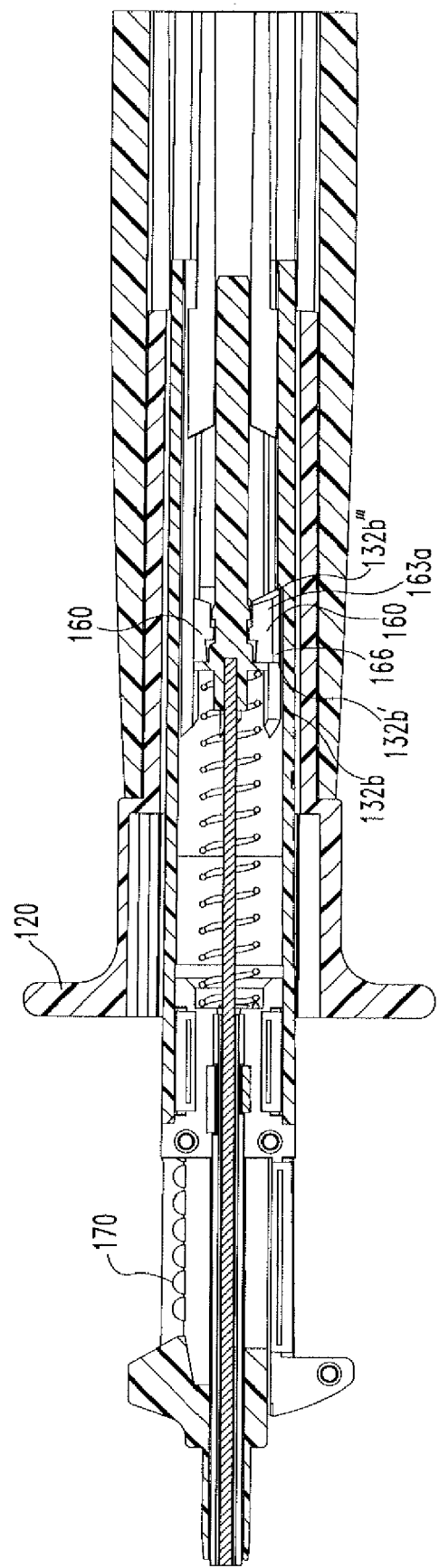

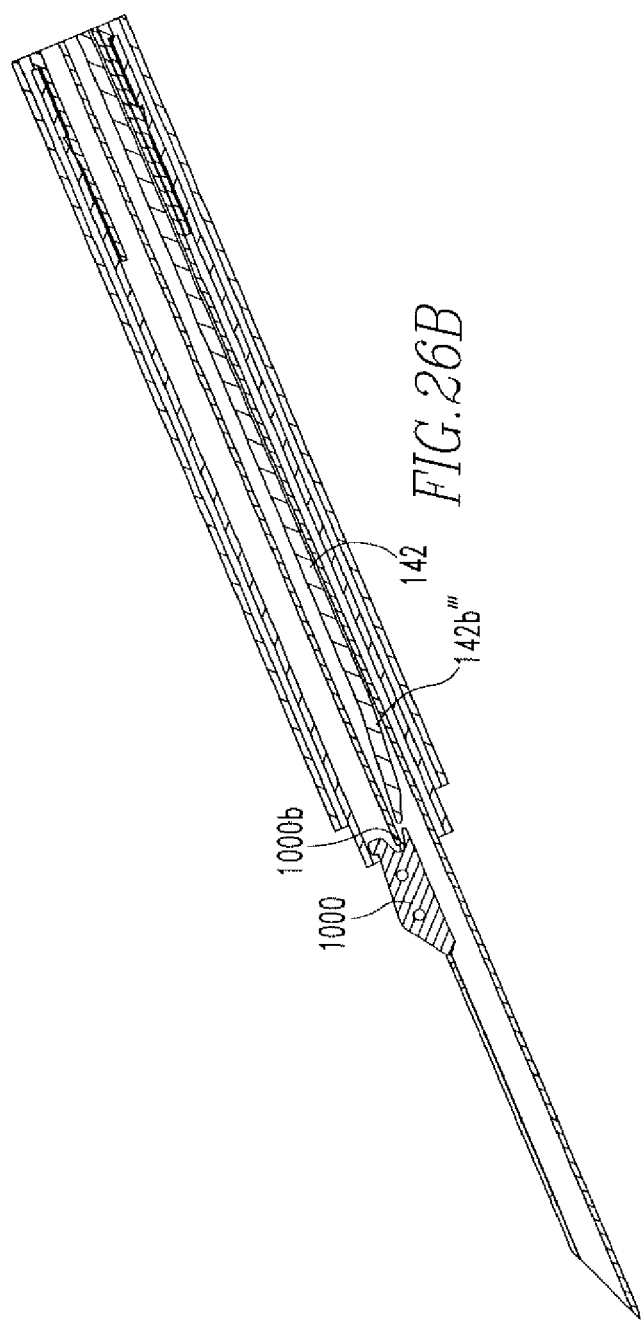

TISSUE REPAIR DEVICE

CROSS-REFERENCE TO RELATED APPLICATIONS

This application is a continuation of U.S. application Ser. No. 16/506,181, filed on Jul. 9, 2019, entitled TISSUE REPAIR DEVICE, which in turn is a continuation of U.S. application Ser. No. 15/391,287, filed on Dec. 27, 2016, now U.S. Pat. No. 10,390,815, which in turn is a continuation of U.S. application Ser. No. 14/242,171, filed on Apr. 1, 2014, now U.S. Pat. No. 9,549,725, which in turn is a continuation of U.S. application Ser. No. 12/623,930, filed on Nov. 23, 2009, now U.S. Pat. No. 8,888,798, which in turn claims priority to and benefit of U.S. Provisional Application No. 61/255,995, filed on Oct. 29, 2009, U.S. Provisional Application No. 61/166,907, filed on Apr. 6, 2009, and U.S. Provisional Application No. 61/117,987, filed on Nov. 26, 2008. This application incorporates the entire contents of the above-identified applications herein by reference in their entirety for all purposes.

BACKGROUND

Field of Technology

The present disclosure relates to devices and methods for repairing tissue.

Related Art

Areas in the body where tissue can be surgically reattached to bone or can be surgically repaired when a tear forms in the tissue include, but are not limited to, the biceps tendon, the lateral collateral ligament in the knee, the medial collateral ligament in the knee, the meniscus in the knee, the popliteal ligament in the leg, and the labrum tendon in the knee.

Fibrous tissue wounds, such as muscle, ligament, and meniscal tears, can be repaired arthroscopically using sutures. Traditionally, to close a fibrous tissue wound, a surgeon would insert two suture needles into the tissue with sutures attached, thread the sutures across the wound and then tie knots to fix the free ends of the sutures within the tissue.

To simplify the wound closure and to improve fixation, various types of devices, and tools for use in delivering the devices, have been developed. One example of a device is the FAST-FIX™ device, which is designed to repair tears in soft tissue, such as the meniscus. This device, and other devices for use in wound closure, is shown and described in U.S. Pat. No. 7,153,312, US Patent Application Publication 2003/0130694 US Patent Application Publication US 2005/0283192, and US Patent Application Publication 2005/0033363, the disclosures or which are incorporated herein by reference in their entireties.

SUMMARY

In one aspect, the present disclosure relates to a tissue repair device. The device includes a handle having a knob coupled to the handle, a needle coupled to the handle, the needle including a proximal end and a distal end, the distal end including a slot, wherein a first anchor is housed within the distal end and a second anchor is housed within the slot and located proximal to the first anchor, and an actuator disposed within the needle and operatively coupled to the knob, wherein advancement of the knob allows for engagement of the actuator with the first anchor and subsequent advancement of the first anchor via the actuator.

In another aspect, the present disclosure relates to a method of tissue repair. The repair includes providing a tissue repair device comprising a handle, a knob coupled to the handle, a needle coupled to the handle, a first anchor and a second anchor coupled to the needle, the first anchor coupled to the second anchor via a flexible member, and an actuator disposed within the needle and operatively coupled to the knob; inserting the needle through tissue, the tissue including a tear, the needle being inserted through the tissue on one side of the tear; advancing the knob of the device to engage the actuator with the first anchor and advance the first anchor out of the needle; removing the needle from the tissue and re-inserting the needle, through the tissue on an opposite side of the tear; advancing the knob of the device to engage the actuator with the second anchor and advance the second anchor out of the needle; and removing the needle from the tissue and reducing a length of the flexible member between the first and second anchor to bring sides of the tear into juxtaposition.

Further areas of applicability of the present disclosure will become apparent from the detailed description provided: hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments, of the present disclosure and together with the written description serve to explain the principles, characteristics, and features of the disclosure. In the drawings:

FIGS. 8A-8B show advancement of the knob of the tissue repair device of FIG. 1 during the method of tissue repair.

FIG. 12B shows a cross-sectional view of the tubing of FIG. 12A.

FIG. 17B shows an isometric view of the distal end of the needle assembly of FIG. 17A.

FIG. 24B shows another isometric view of the distal end of the tissue repair device FIG. 24A without sutures.

FIG. 24C shows a cross-sectional view of the distal end of the tissue repair device of FIGS. 9A 9C.

FIG. 24D shows a cross-sectional view of the tissue repair device of FIGS. 9A-9C, specifically the pusher assembly prior to deployment of the first anchor.

FIG. 26B shows a cross-sectional view of the distal end of the tissue repair device of the present disclosure alter deployment of the first anchor and prior to deployment of the second anchor.

DETAILED DESCRIPTION OF TUE EMBODIMENTS

The following description of the preferred embodiment(s) is merely exemplary in nature and is in no way intended to limit the disclosure, its application, or uses.

Figure 1:
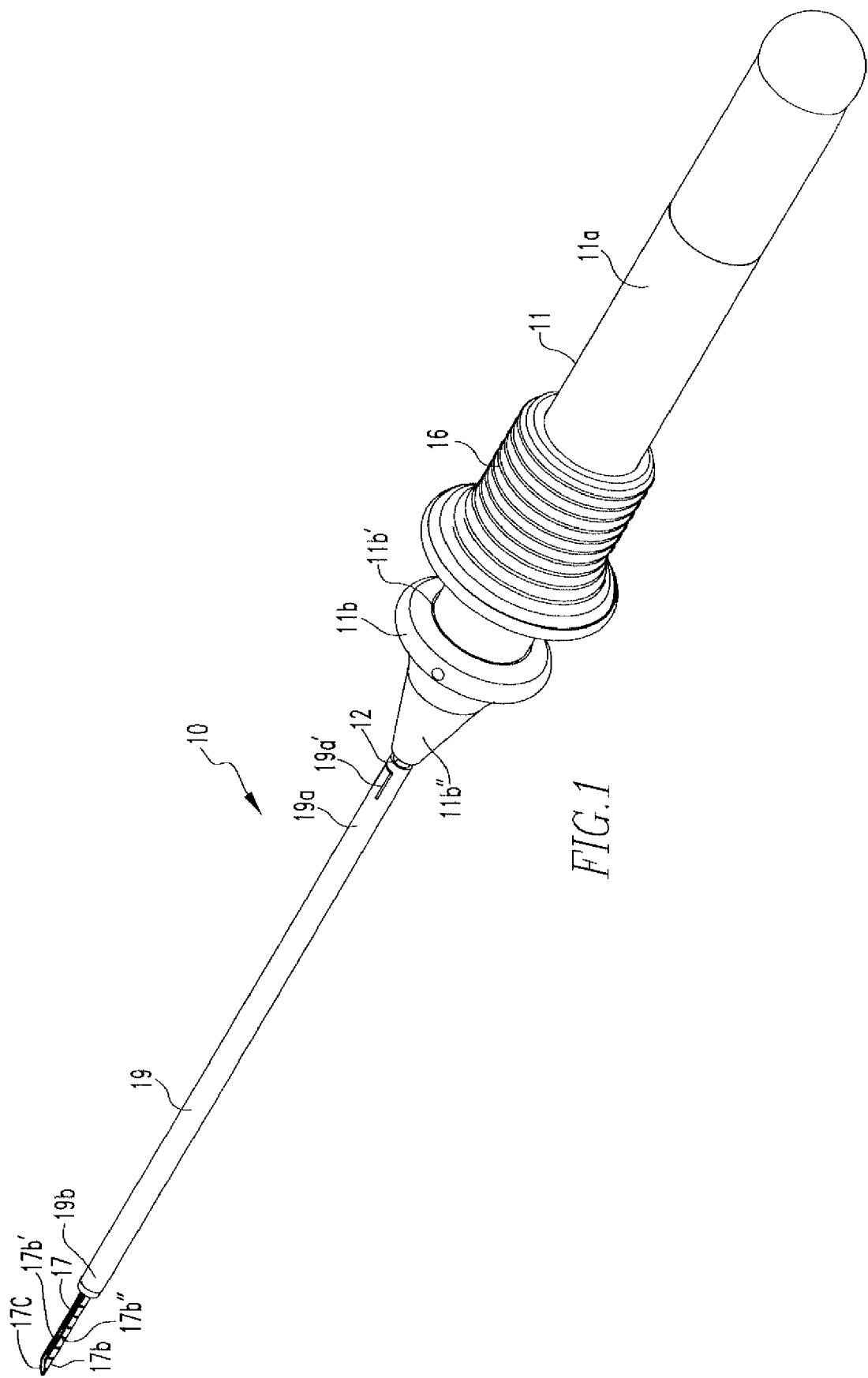
FIG. 1 shows a perspective view of a First embodiment of the tissue repair device of the present disclosure.
Figure 2:
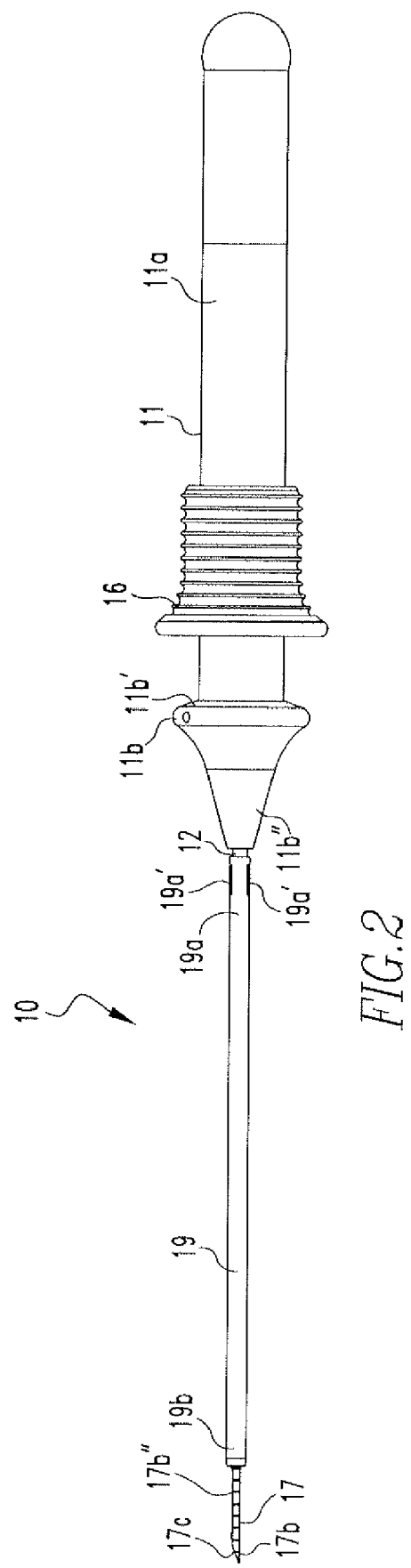
FIG. 2 shows a side view of the tissue repair device of FIG. 1.
Figure 3:
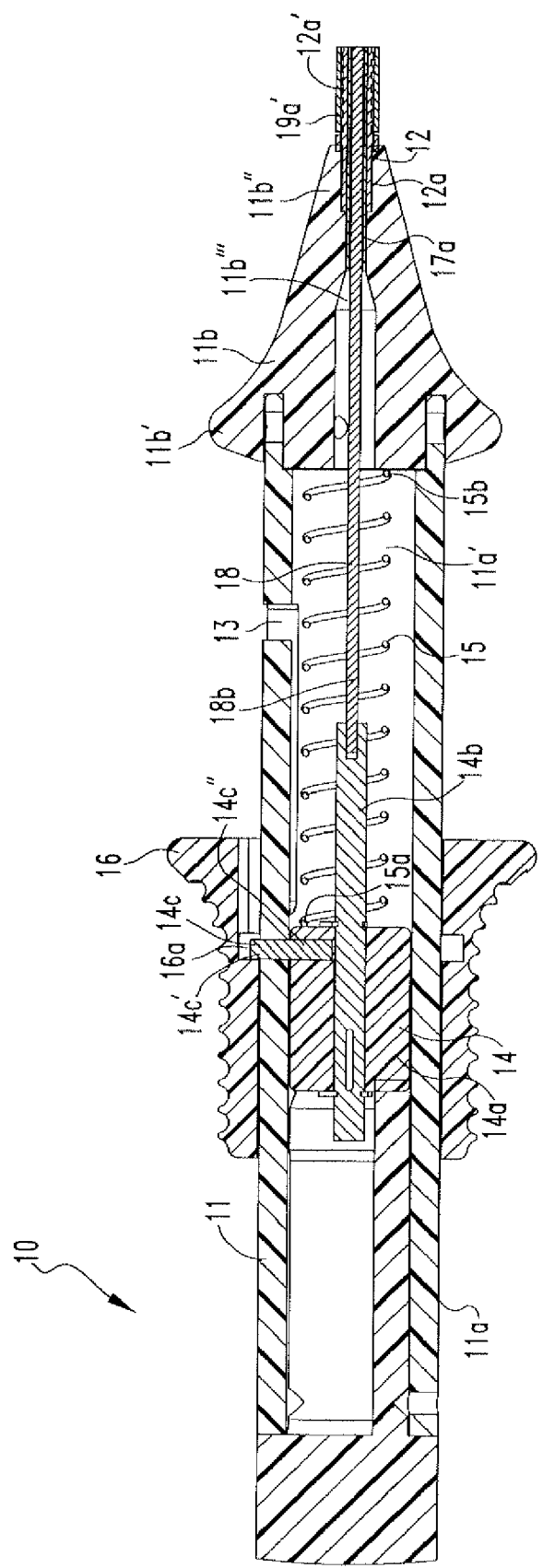
FIG. 3 shows a cross-sectional view of the handle of the tissue repair device of FIG. 1.
Figure 4:
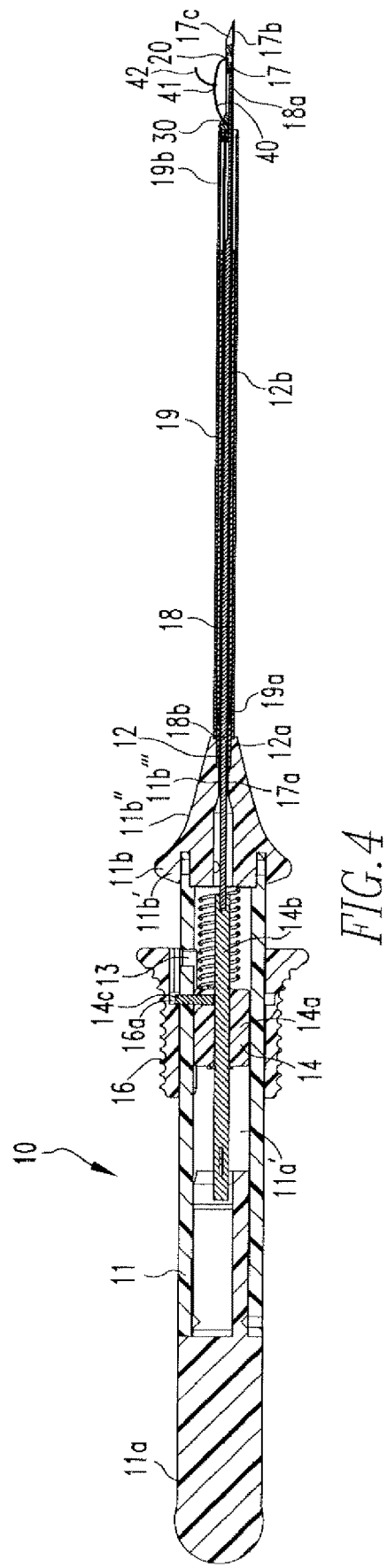
FIG. 4 shows a cross sectional view of the tissue repair device of FIG. 1.
Figure 5:
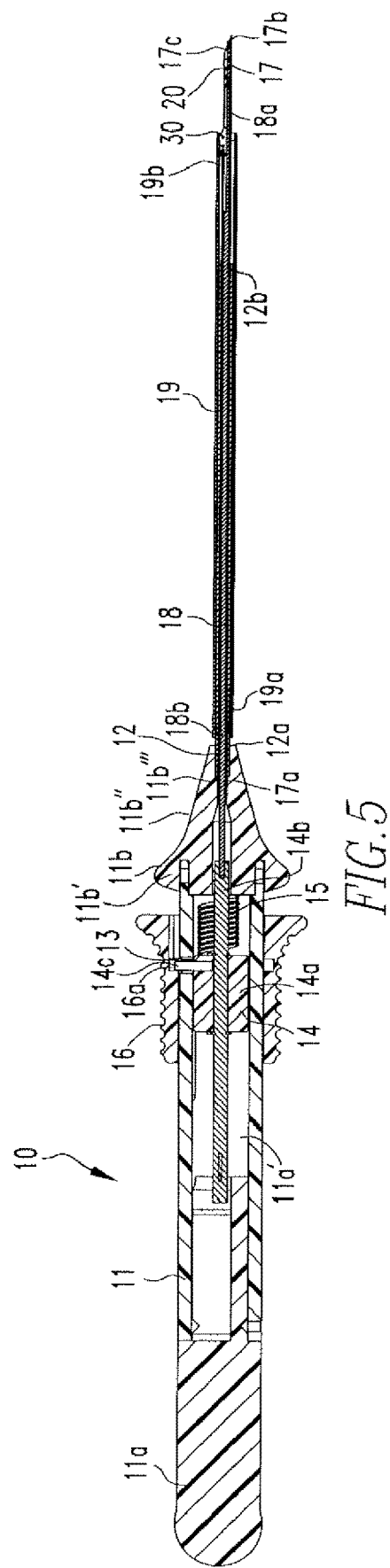
FIG. 5 shows another cross sectional view of the tissue repair device of FIG. 1.

FIGS. 1-5 show a first embodiment the soil tissue repair device 10 of the present disclosure. The device 10 includes a handle 11 and a cannula 12 coupled to the handle 11. The handle 11 includes a body 11a as and a nose cone 11b coupled to the body 11a. The nose cone 11b includes a proximal end 11b' and a distal end 11b''. The body 11a includes a cavity 11a' and a J-shaped channel 13 (FIGS. 1 & 8A-8B). The channel 13 includes a first portion 13a and a second portion 13b. A pusher 14 is housed within the cavity 11a'. The pusher 14 includes a body 14a, a shaft 14b coupled to the body 14a, and a pin 14c coupled the body 14a. The pin 14c includes a distal portion 14c' that extends through the channel 13 and a proximal portion 14c'' that is coupled to the body 14a. In addition, the cavity 11a' includes a coil 15, wherein one end 15a of the coil 15 is coupled to the pusher body 14a and the other end 15b of the coil 15 is coupled to the proximal end 11b' of the nose cone 11b, as shown in FIG. 3. Furthermore, a knob 16 is disposed on the body 11a of the handle 11. The knob 16 includes an aperture 16a that houses the distal portion 14c' of the pin 14c. The coil 15, as shown in FIG. 3, is in a released position when the knob 16 is in a starting position and becomes compressed when the knob 16 is advanced toward the nose cane 11b, as shown in FIGS. 4 & 5.

Figure 6A:
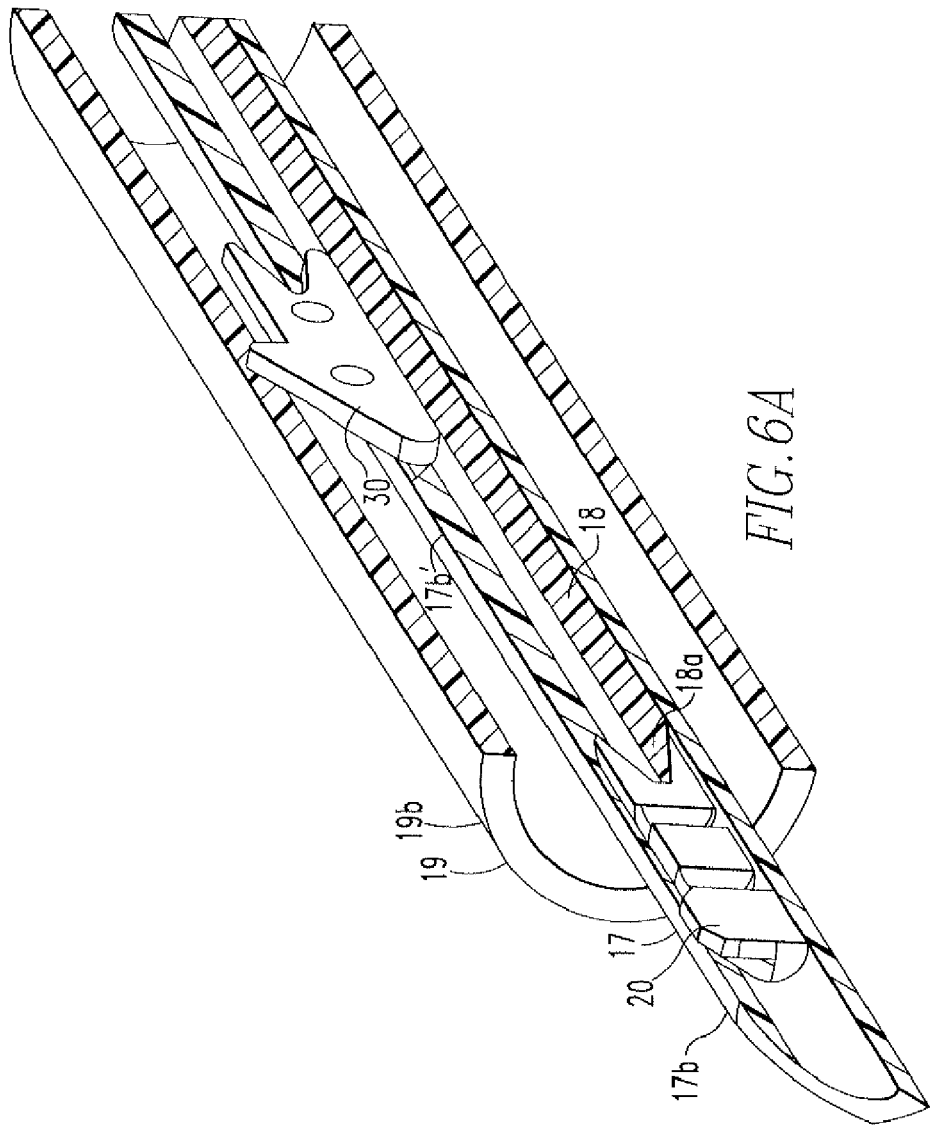
FIGS. 6-6B show a cross-sectional view and a perspective view of the distal end of the needle of the tissue repair device of FIG. 1.
Figure 6B:
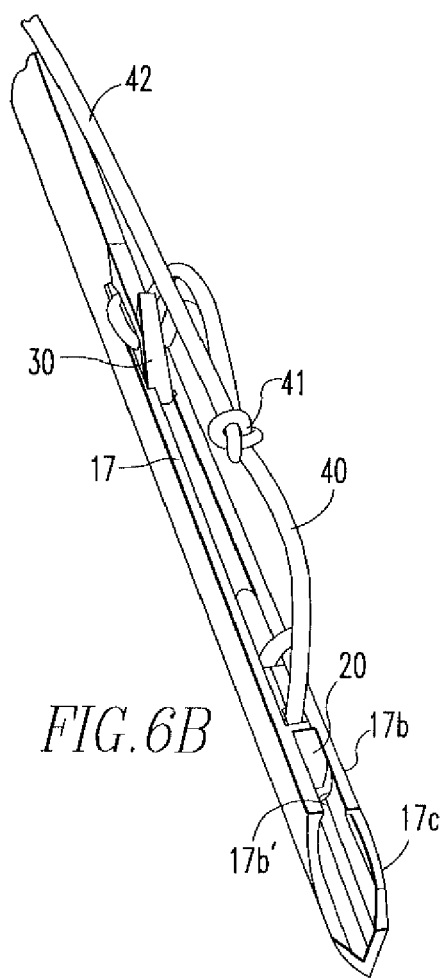

The cannula 12 includes a proximal end 12a and a distal end 12b. The proximal end 12a is partially housed within a through hole 11b''' of the nose cone 11b and includes areas of reduced diameter 12a'. A needle 17 is disposed within the cannula 12 and includes a proximal end 17a and a distal end 17b. The proximal end 17a is partially housed within the through hole 11b''' of the nose cone 11b and the distal end 17b includes a beveled, pointed tip 17c and a slot 17b'. As shown in FIGS. 6A and 6B, a first anchor 20 is housed within the distal end 17b of the needle 17 and a second anchor 30 is housed within the slot 17b' and located proximal to the first anchor 20. The anchors 20,30 are coupled via a flexible member 40, such as a suture, that includes a slip knot 41 located between the anchors 20, 30. The suture 40 is coupled to the anchors 20, 30 and the slip knot 41 is Conned via the methods described in the above incorporated US patents and published applications. A free end 42 extends from the slip knot 41 and the suture length between the anchors 20,30 is reduced upon pulling the free end 42 in one direction, hut not in another direction, as will be further described below.

The distal end 17b also includes laser marks 17b'' that are used during repair to indicate the depth of the needle 17, as will be further described below. An actuator 18 is disposed within the needle 17 and includes a distal end 18a engaged with the first anchor 20 and a proximal end 18b coupled to the pusher shaft 14b. A depth indicator 19 is disposed over the cannula 12 and the needle 17. The indicator 19 includes a proximal end 19 and a distal cod 190. The proximal end 19a includes at least two tabs 19a' that engage the areas of reduced diameter 12a' and couple the indicator 19 to the cannula 12. Prior to repair, the indicator 19 is coupled to the cannula 12 such that the distal end 19b covers the distal end 170 of the needle 17. FIG. 6A shows the distal ends 170,190 of the needle 17 and the indicator 19. As shown, the first anchor 20 is within the distal end 170 of the needle 17 and the second anchor 30 is within the opening 17b', such that the actuator 18 is located below the second anchor 30 and the distal end 18a is in engagement with the first anchor 20.

Figure 7A:
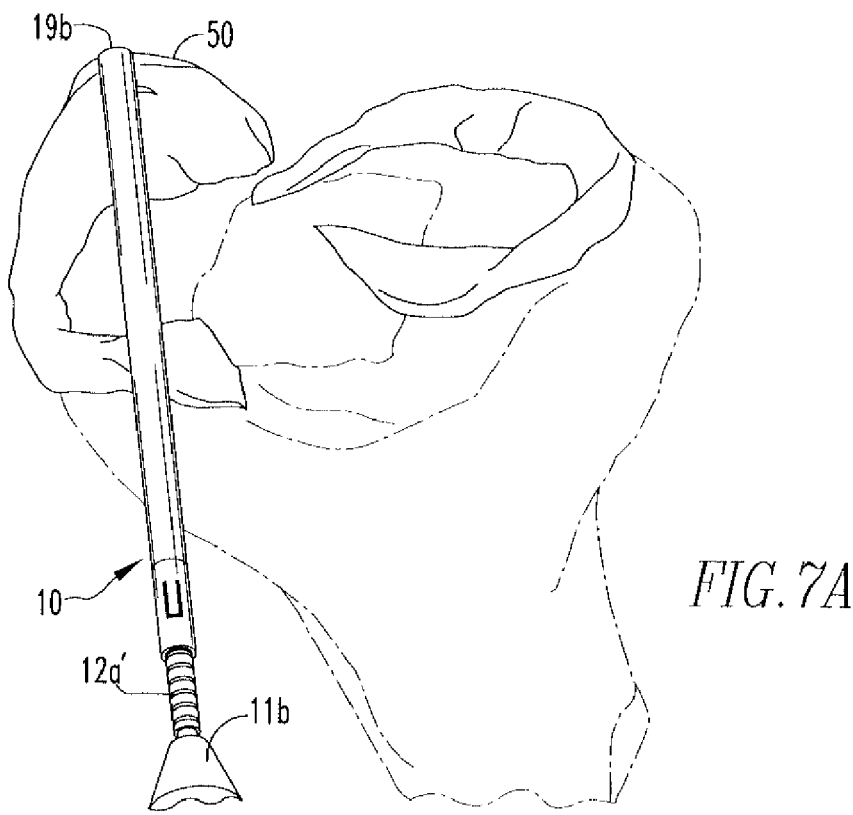
FIGS. 7A-7E show a method of tissue repair via use of the tissue repair device of the present disclosure.
Figure 7B:
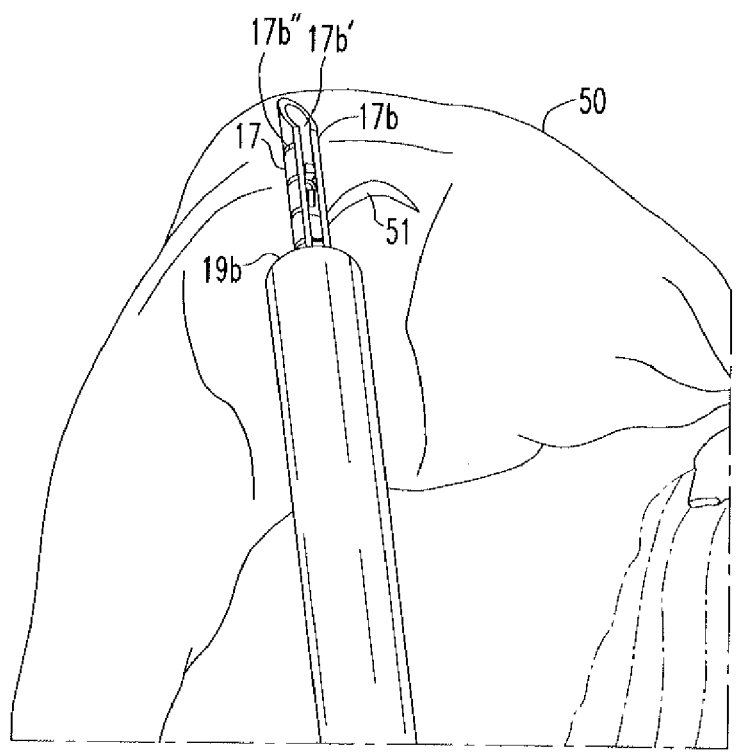
Figure 7C:
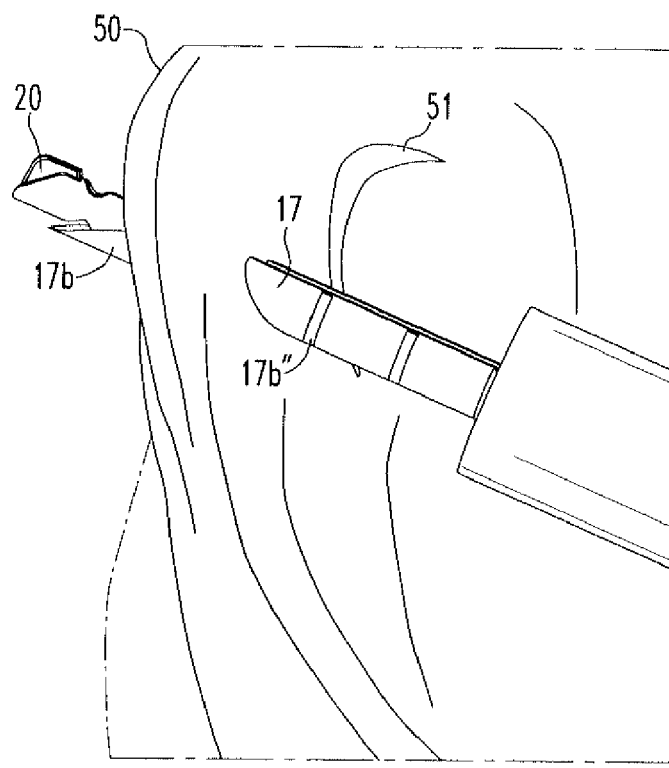

Referring to FIGS. 7A-7E, in use, preferably under arthroscopic guidance, the user inserts the device 10 into, for example, the knee joint, until the distal end 190 ache indicator 19 is in contact with the superior surface of the meniscus 50, as shown in FIG. 7A. The indicator 19 is then moved proximally toward the nose cone 110 to uncover the distal end 17b of the needle 17, and determine the appropriate needle insertion depth, as shown in FIG. 7b. In practice, enough of the needle 17 should be exposed to allow for insertion of the needle 17 through the meniscus and subsequent delivery of the anchor 20, but not so much that the needle 17 will extend into areas behind the meniscus, such as neurovascular areas, where it could cause damage. Insertion of the end 17b through the meniscus 50 occurs until the appropriate laser mark 17b" is reached and the knob 16 is then moved distally toward the nose cone 110 to deploy the first anchor 20, as shown in FIG. 7C. Before deployment of the first anchor 20, the pin 14c is located in the first portion 13a of the channel 13, as shown in FIG. 8A. However, after deployment of the first anchor 20, the pin 14c is located in the second portion 13b oldie channel 13, as shown in FIG. 8B.

Figure 7D:
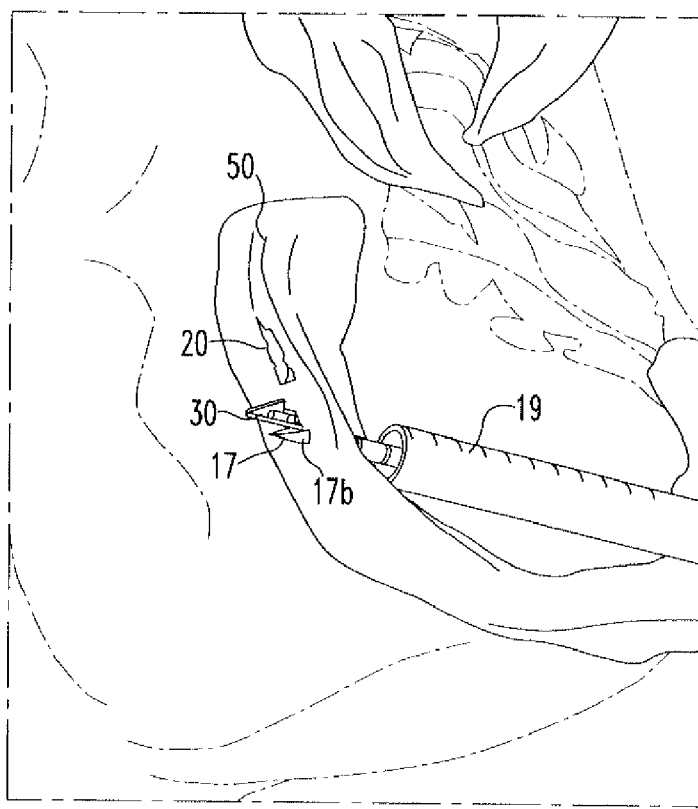
Figure 7E:
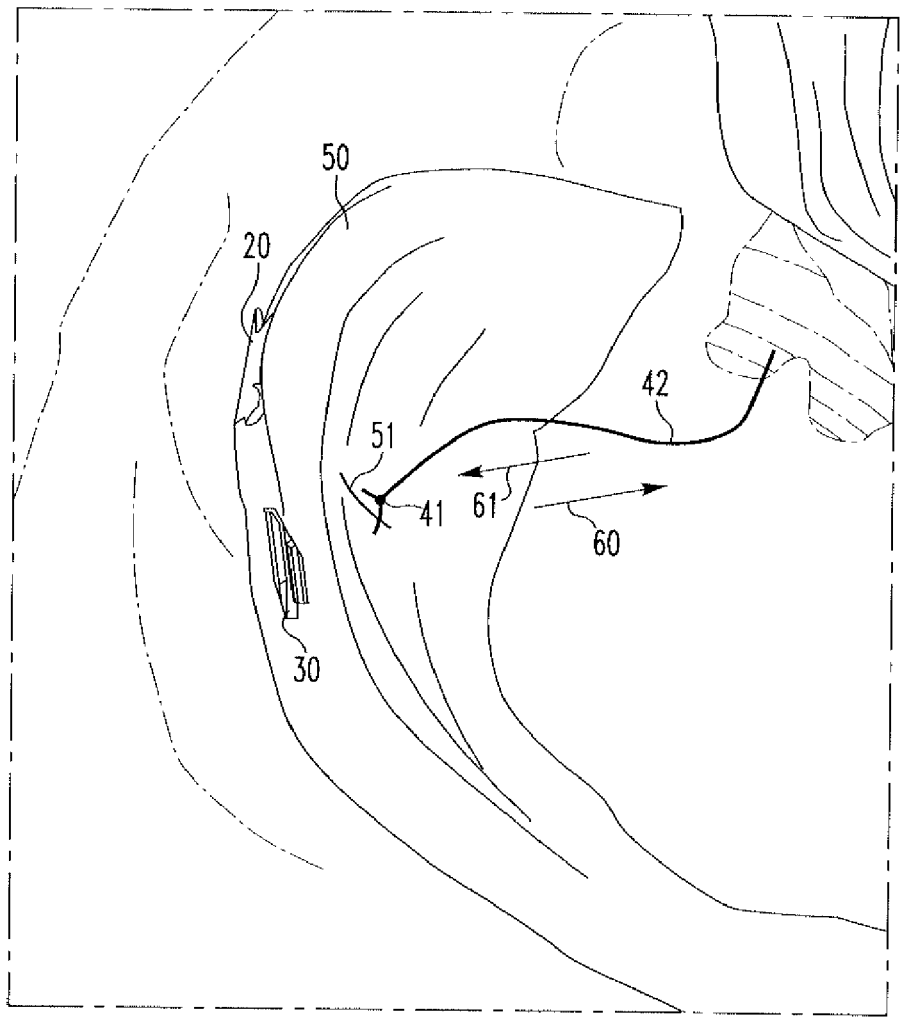

Once the first anchor 20 has been deployed, the needle 17 is removed from the meniscus 50 and re-inserted across the tear 51, as shown in FIG. 7D. The knob 16 is, once again, moved distally toward the nose cone 11b to deploy the second anchor 30. The device 10 is subsequently removed from the knee joint and the free end 42 is pulled in the direction of arrow 60. This shortens the length of suture between anchors 20,30, bringing sides of tear 51 into juxtaposition, as shown in FIG. 7E. Depending on the length of suture between anchors 20,30, the slip knot 41 will either be on the tissue suture or move within the tissue 50. Slip knot 41 allows the suture 40 to slide in the direction of arrow 61, but does not allow the suture 40 to slide in the opposite direction 60. The tension placed on suture 40 by pulling on the suture 40 relative to anchors 20,30 acts to turn the anchors 20,30 such that their long sides am in contact with tissue surface. Excess suture 40 can then be cut off. Further manipulation of suture 40 is not needed to secure anchors 20,30, although the surgeon may wish to provide additional fastening as a back-up securement measure.

For the purposes of this disclosure, the handle 11, nose cone 11b, pusher 14, shaft 14b, knob 16, actuator 18, cannula 12, and depth indicator 19 are of a non-metal material, but may be made from a metal material. In addition, the coil 15, pin 14c, and needle 17 are of a biocompatible metal material, such as stainless steel. The anchors 20,30 and suture 40 are of a non-metal material, such as a polymer material, and may or may not be absorbable. The handle 11 and nose cone 11b may be coupled via mechanical means, adhesive means, such as a non-toxic, biocompatible, adhesive glue, or other means known to one of skill in the art, in addition, the cannula 12 and noodle 17 are coupled to the nose cone 11b, the actuator 18 is coupled to the shalt 14b and the coil 15 is coupled to the nose cone 11b and the pusher 14 via similar means. The device 10 and its components are all made via a method known to one of skill in the art.

Figure 9A:
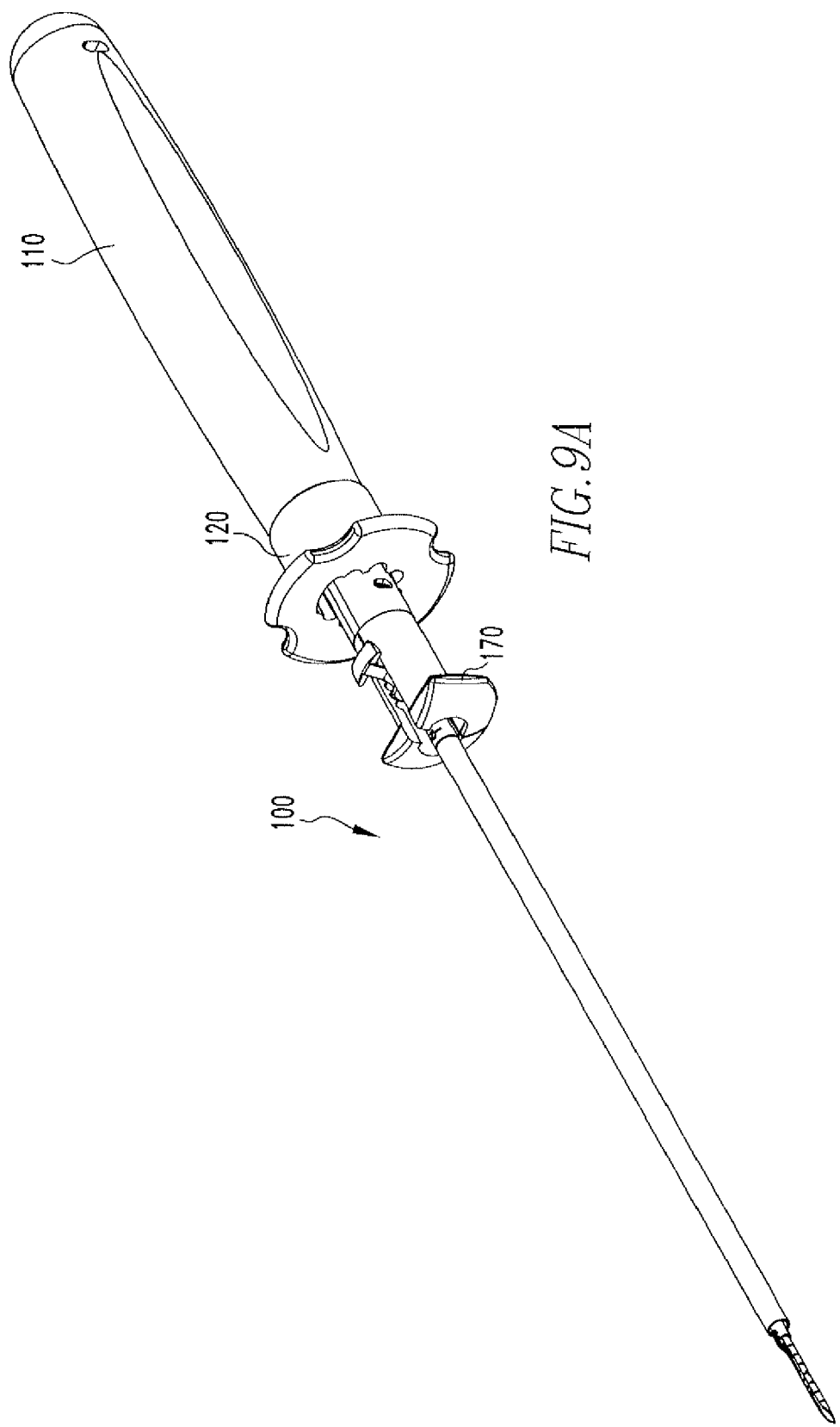
FIG. 9A shows a perspective view of an a second embodiment of the tissue repair device of the present disclosure.
Figure 9B:
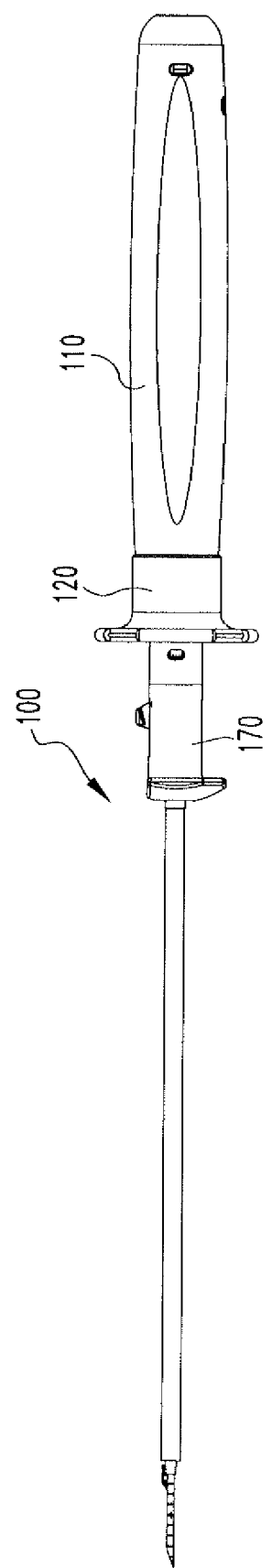
FIG. 9B shows a side view of the tissue repair device of FIG. 9A.
Figure 9C:
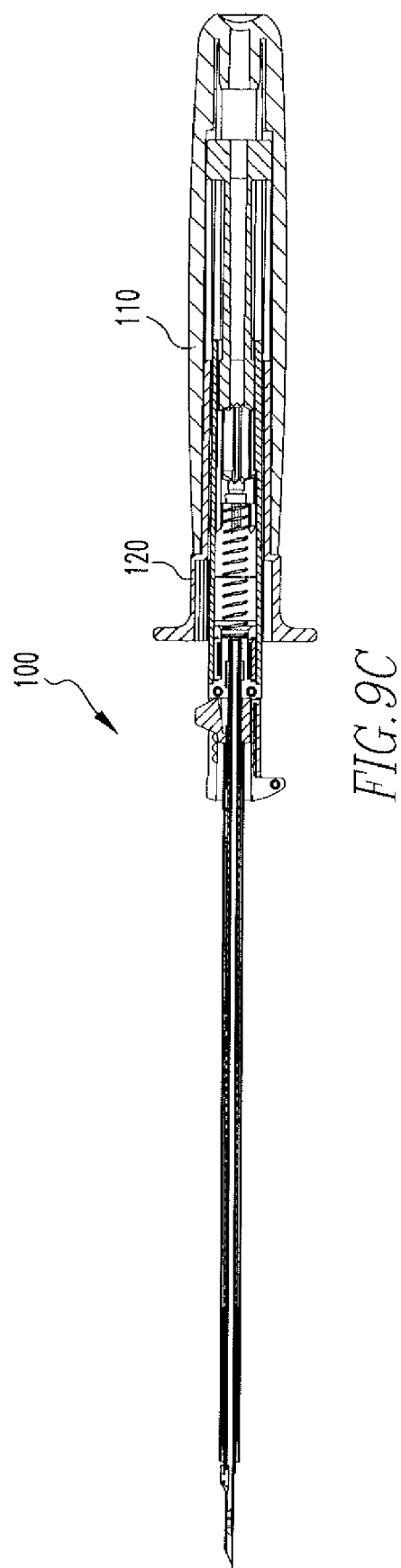
FIG. 9C shows a cross-sectional side view of the tissue repair device of FIG. 9A.
Figure 10:
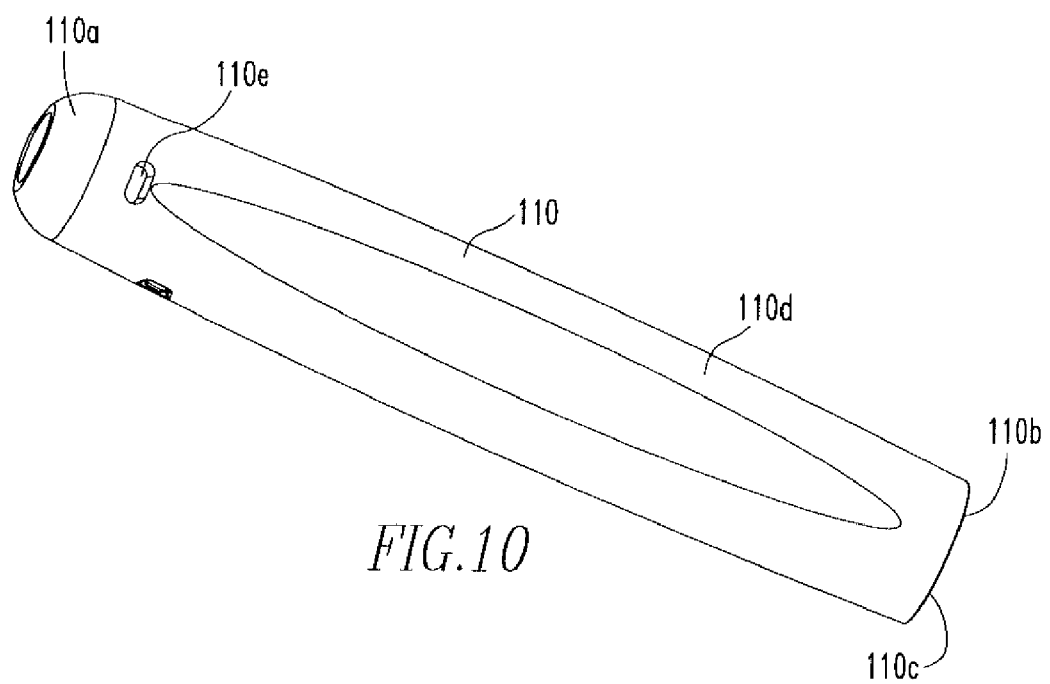
FIG. 10 shows an isometric view of the handle of the tissue repair device of FIGS. 9A-9C.
Figure 11A:
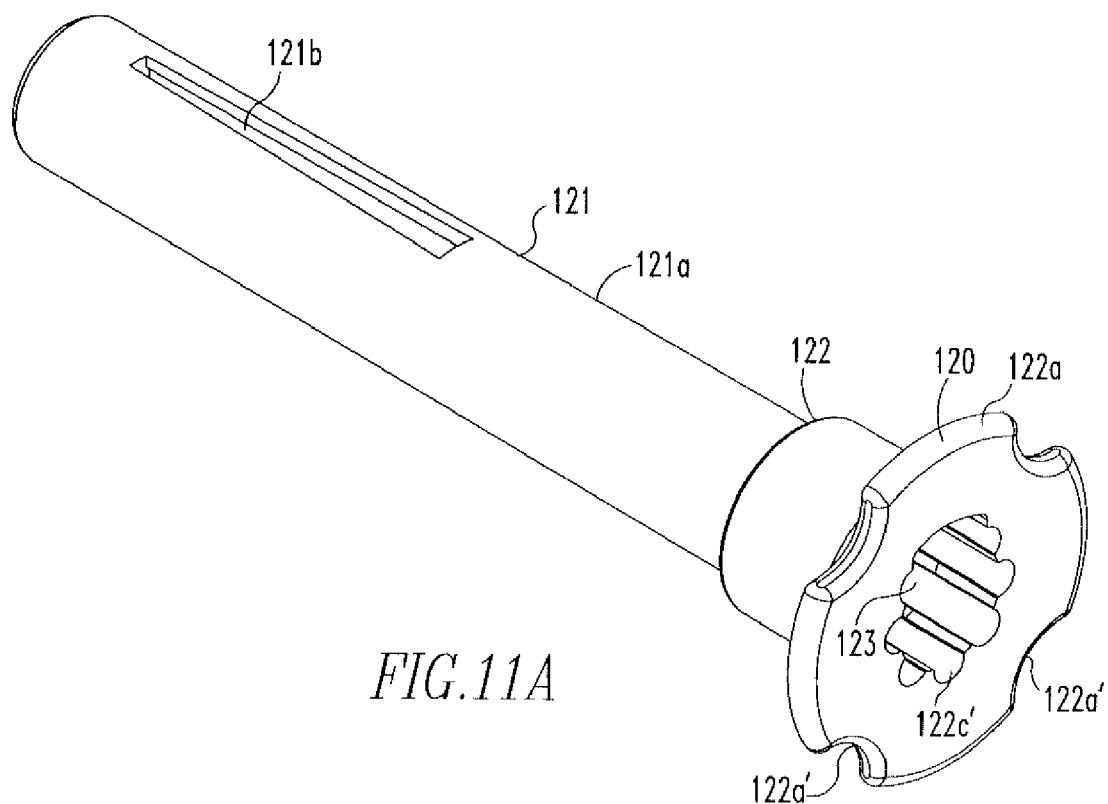
FIG. 11A shows an isometric view of the knob of the tissue repair device of FIGS. 9A-9C.
Figure 11B:
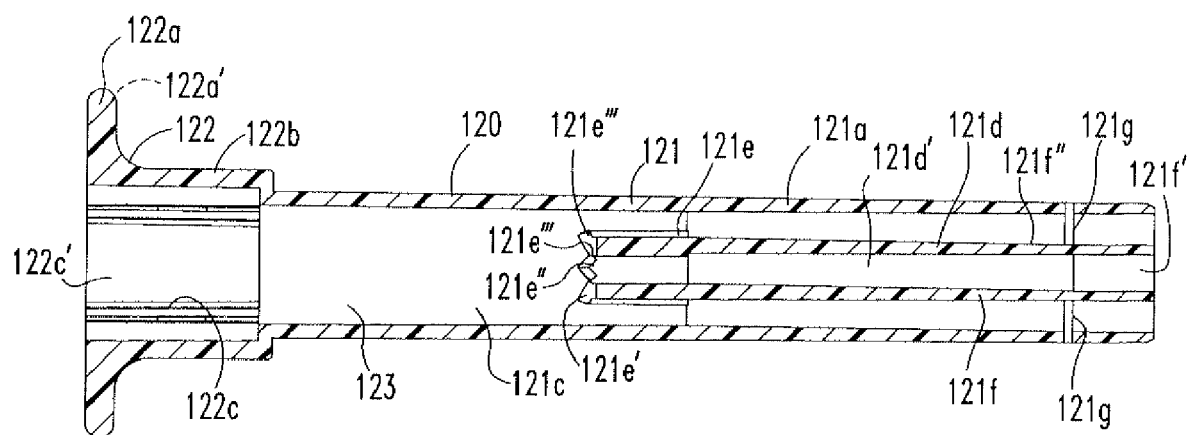
FIG. 11B shows a cross-sectional view of the knob of FIG. 11A.

FIGS. 9A-9C show an alternative embodiment of the soft tissue repair device 100 of the present disclosure. The components of the device 100 will be described with reference to FIGS. 10, 11A-11B, 12A-12B, 13A-13B, 14, 15, 16A-16C, 17A-17B, 18A-18B, 19, 20, 21A-21B, 22A-22B, and 23. The device 100 includes a handle 110 which, as shown in FIG. 10, includes a closed-ended proximal portion 110a, an open distal portion 110b, a cannulation 110c, and an outer surface 110d including holes 110e on opposite sides of the handle 110. The purpose of the holes 110e will be further described below. Disposed within the handle 110 is a knob 120. As shown in FIGS. 11A-11B, the knob 120 includes a shall 121, a bead 122 coupled to the shaft 121, and a cannulation 123. The head 122 includes a flange 122a and a neck 122b, both of which have a larger diameter than the shaft 121. The flange 122a includes depressions 122a'. The inner wall 122e of the head 122 includes several grooves 122c'. The shaft 121 includes an outer wall 121a having slots 121b and an inner wall 121c. Coupled to the inner wall 121c is a rod 121d having a cannulation 121d'. The cannulation 121d' has a "D" shape, such that a portion of the cannulation 121d' is flat and the rest of the cannulation is rounded. The rod 121d includes a first portion 121e and a second portion 121f. The first portion 121e includes a face 121e' having spikes 121e" and divots 121e"' located between the spikes 121e"'. An end 121f' of the second portion 121f includes legs 121g that extend between an outer surface 121f" the second portion 121f to an inner wall 121e of the shaft 121.

Figure 12A:
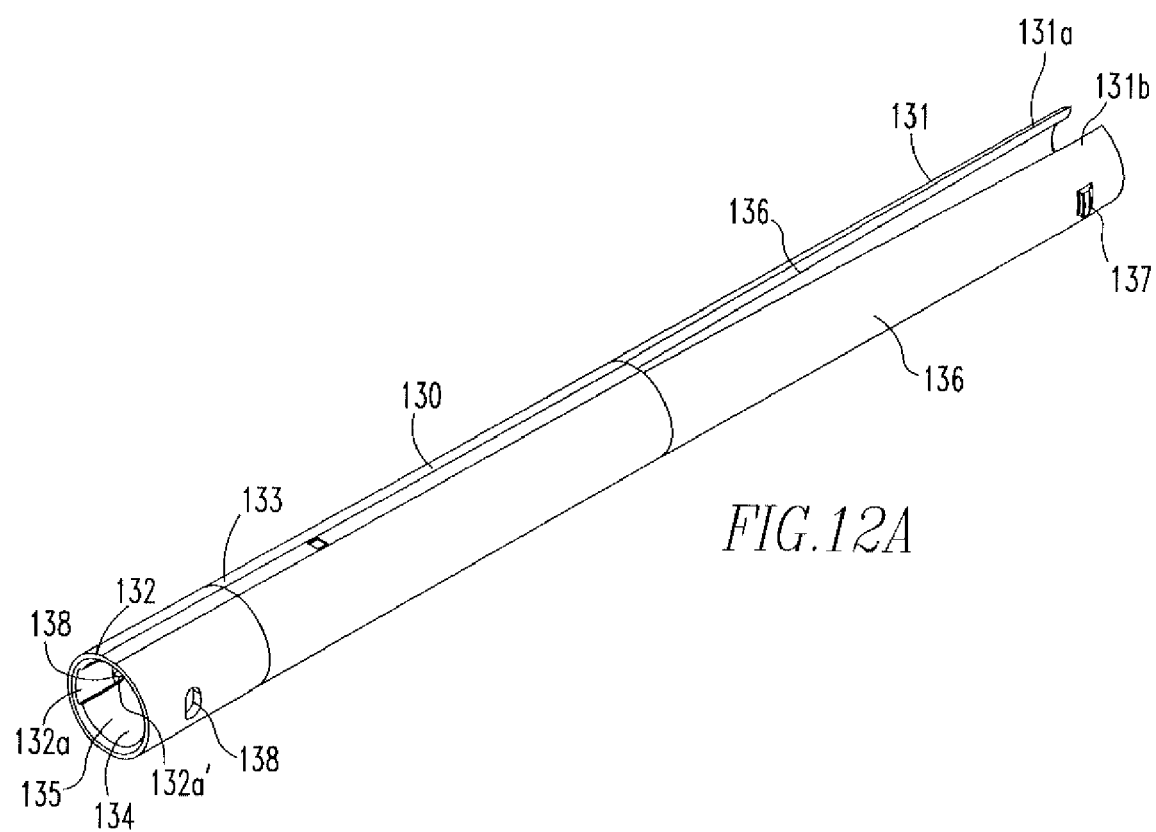
FIG. 12A shows an isometric view of the tubing of the tissue repair device of FIGS. 9A-9C.

Disposed within the cannulation 123 of the knob 120 and, therefore the handle 110, is a tubing 130. As shown in FIGS. 12A-12B, the tubing 130 includes a proximal portion 131, a distal portion 132, an outer surface 133, an inner surface 134, and a cannulation 135. The proximal portion 131 of the tubing 130 includes slots 136 that divide the proximal portion 131 into two sides 131a,131b. Both sides 131a,131b of the proximal portion 131 include tabs 137 that extend outward from the outer surface 133 of the tubing 130. When the tubing 130 is disposed within the handle 110, the tabs 137 are disposed within the holes 110e of the handle 110, thereby coupling the tubing 130 to the handle 110. The distal portion 132 of the tubing 139 includes channels 132a located on opposite sides of the distal portion 132. A hole 138 is located at an end 132a' of each channel 132a. The purpose of the channels 132a and the boles 138 will be further described below. The distal portion 132 also includes rails 139 and slots 132b,132c located between the roils 139. Slots 132b,132c both extend an entire length of the rails 139. However, slot 132b includes two regions 132b'. 132b" having different depths, such that a stepped region 132b'" is present along the slot 132b, as is more clearly shown in FIG. 12B.

Figure 13A:
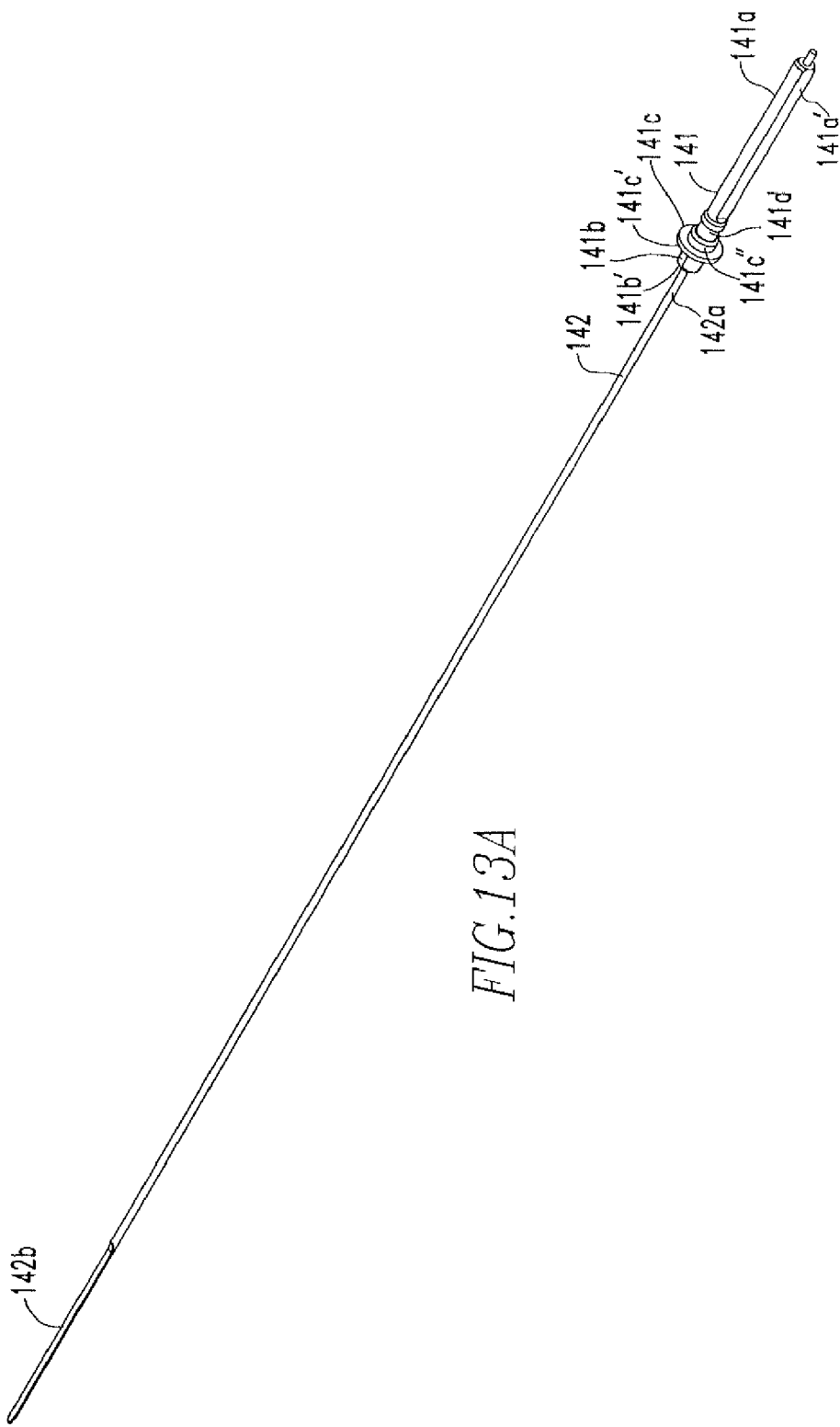
FIG. 13A shows an isometric view of the pusher assembly of the tissue repair device of FIGS. 9A-9C.
Figure 13B:
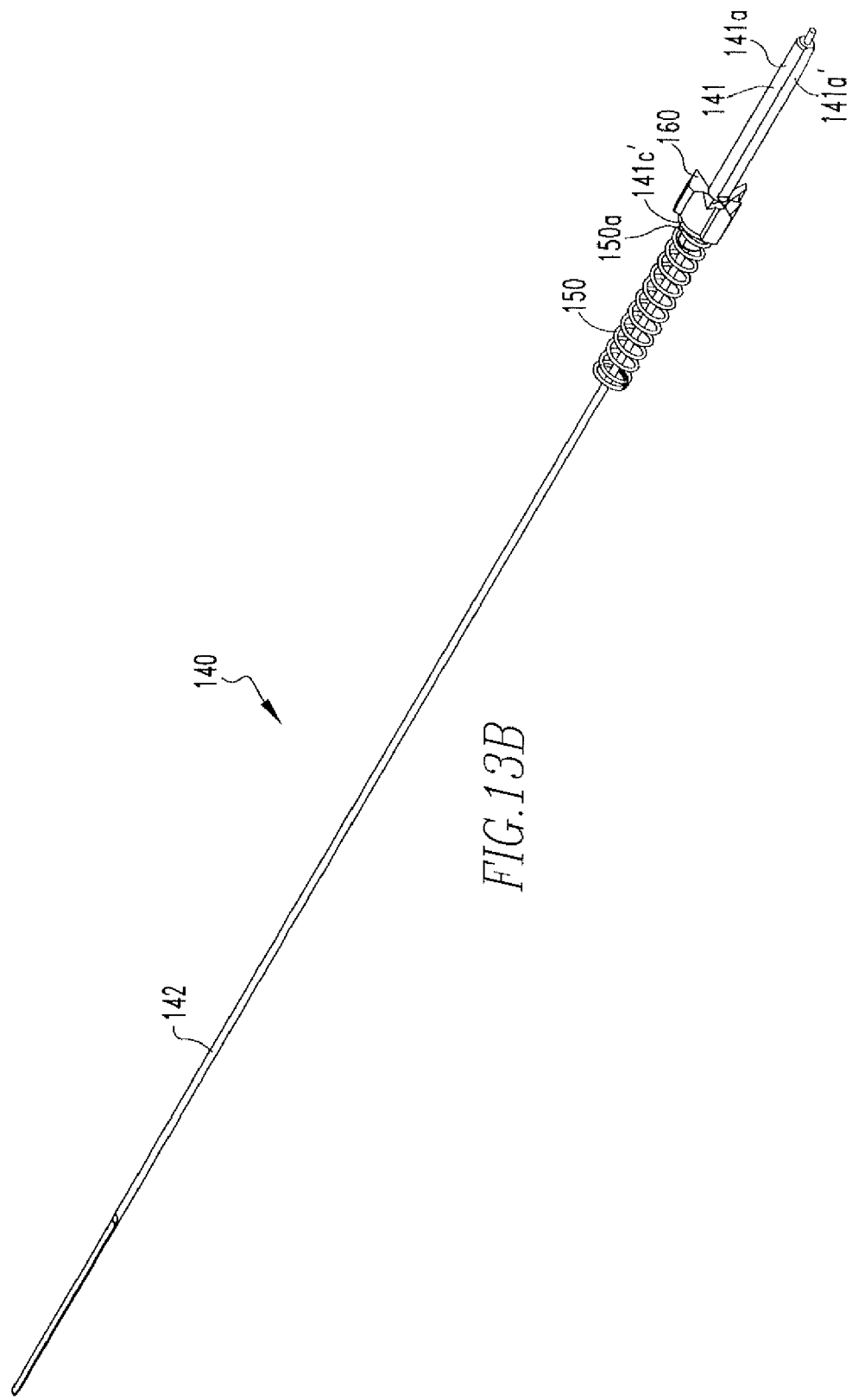
FIG. 13B shows an isometric view of the pusher assembly of the tissue repair device of FIGS. 9A-9C with the pusher disk and coiled spring.

Also disposed within the handle 110 is a pusher assembly 140. The pusher assembly 140 is shown in FIG. 13B. FIG. 13A shows the pusher assembly 140 without the coiled spring 150 or the pusher disk 160. The assembly 140 includes a shaft 141 and an actuator 142 coupled to the shaft 141. The shaft 141 includes a proximal portion 141a and a distal portion 141b. The proximal portion 141a includes a flat portion 141a' such that the proximal portion 141a is in the shape of a "D". As mentioned above, the cannulation 121d' of the rod 121d also has a "D" shape. As is shown in FIG. 9C, the proximal portion 1412 of the shaft 141 is housed within the cannulation 121d' of the rod 121d, such that the flat portions of the cannulation 121d' and the proximal portion 141a are adjacent to each other, thereby coupling the pusher assembly 140 to the knob 120. As will be further described below, during operation, the "D" shapes of the cannulation 121d' and the proximal portion 141a allow for axial movement of the proximal portion 141a within the cannulation 121d' and restrict rotational movement of the proximal portion 141a within the cannulation 121d'.

The distal portion 141b includes a flanged cap 141c located on the distal portion 141b and an inner channel 141b'. The flamed cap 141c includes a cap 141c' and a flange 141c". The flanged cap 141c is located on the distal portion 14115 such that there is an area or reduced diameter 141d located between the proximal portion 141a and the flange 141c". The distal portion 141b as configured for attachment of a pusher disk 160 as will be further described below with regard to FIG. 15.

Figure 14:
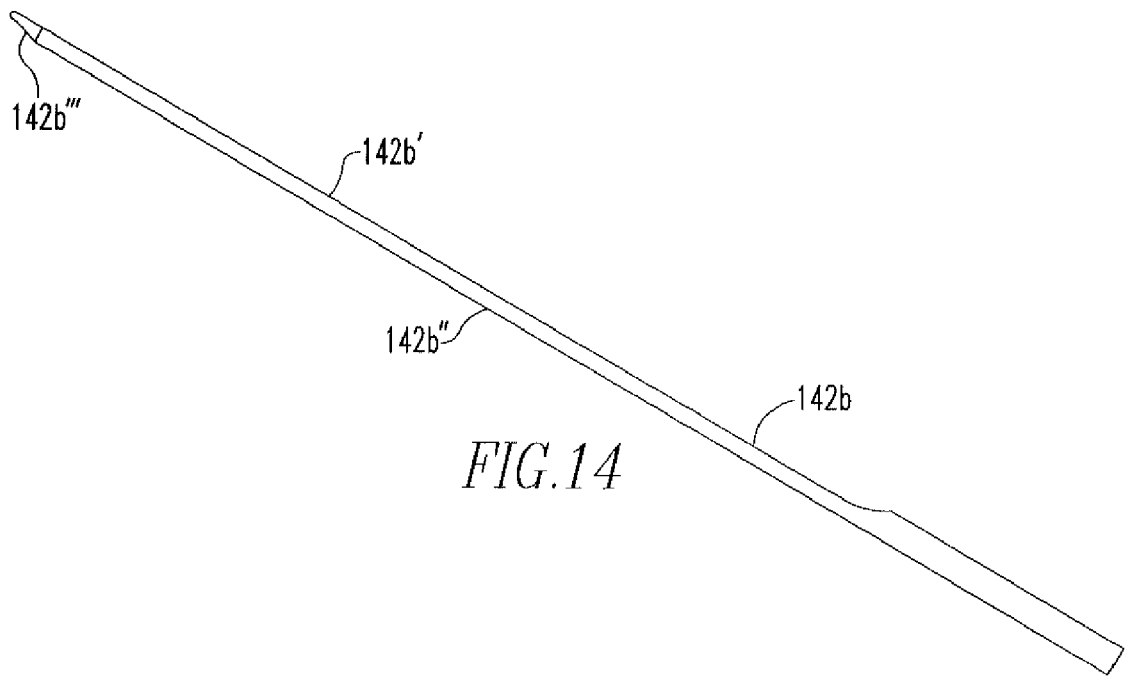
FIG. 14 shows an isometric view of the distal end of the actuator of FIGS. 13A-13B.

The actuator 142 includes a proximal portion 142a and a distal portion 142b. The proximal portion 142a is housed within the inner channel 141b, thereby coupling the actuator 142 to the shaft 141. As shown in FIG. 14, the distal portion 142b of the actuator 142 includes a flat top portion 142b, a rounded bottom portion 142b''', and a beveled end, portion 142b'''. The top portion 142b' and the end portion 142b''' are shaped to engage a tissue anchor, as will be further described below. A coiled spring 150 is disposed on the actuator 142 such that an end 150a of the spring 150 rests against the cap 141c', as shown more clearly in FIG. 13B. As will be further described below, it is important that the end 150a of the spring 150 rest against the cap 141c' rather than the pusher disk 160 so as to not restrict rotation of the pusher disk 160 during operation of the device 100.

Figure 15:
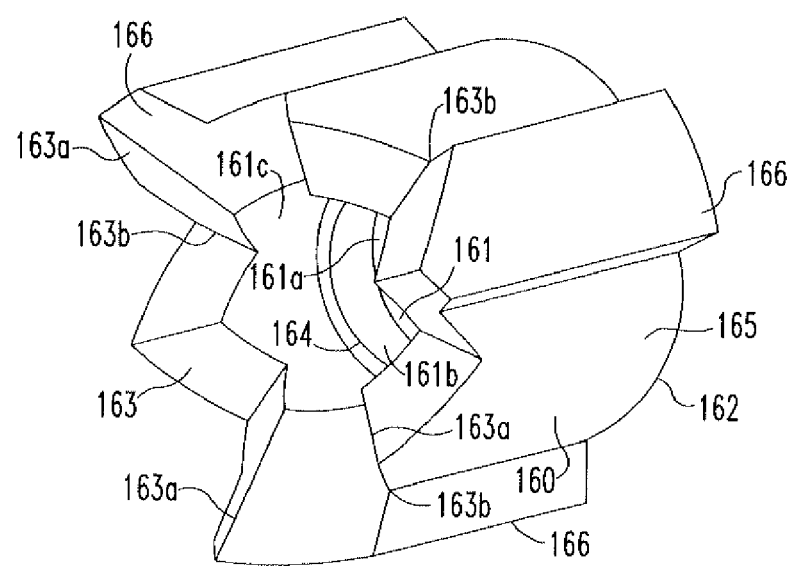
FIG. 15 shows an isometric view of the pusher disk of the pusher assembly of FIG. 13B.

As shown in FIG. 15, the pusher disk 160 includes a cannulation 161, a front portion 162, a back portion 163, an inner surface 164 and an outer surface 165. Protrusions 166 are located on the outer surface 165 of the disk 160. The cannulation 161 includes a first portion 161a, a second portion 161b, and a third portion 161c. The second portion 161b has a smaller diameter than both of the first and third portions 161a,161c, such that coupling of the pusher disk 160 to the distal portion 141b results in the second portion 161b being disposed within the area of reduced diameter 141d. In addition, the first and third portions 161a, 161c are of a diameter such that during operation of the device 100 the disk 160 is capable of rotating without restriction from either the flange 141c'' or the proximal portion 141a. The back portion 163 of the disk 160 includes spikes 163a and divots 163b located between the spikes 163a. During operation of the device 100, the spikes 163a and divots 1631) engage the spikes 121e'' and divots 121e''' of the rod 121d and the rails 139 of the tubing 130, as will be further described below. In addition, during operation, the protrusions 166 slide within the slots 132b,132e of the tubing 130, as will be further described below.

Figure 16A:
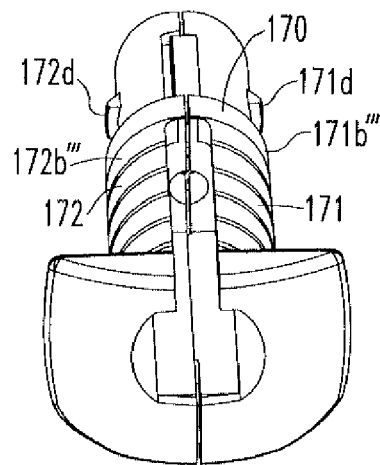
FIG. 16A shows an isometric view of the hub of the tissue repair device of FIGS. 9A-9C.
Figure 16B:
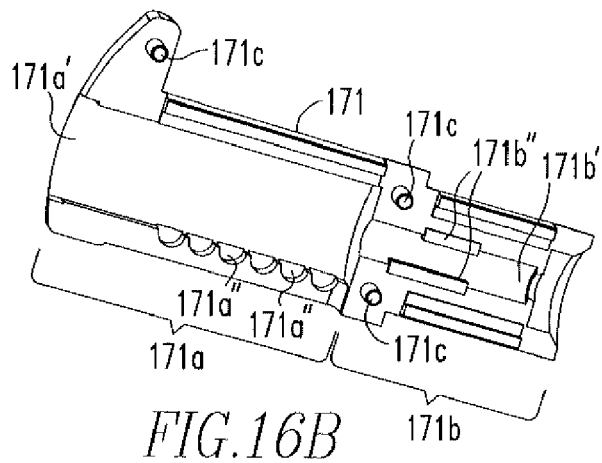
FIG. 16B shows an isometric view of a first part of the hub of FIG. 16A.
Figure 16C:
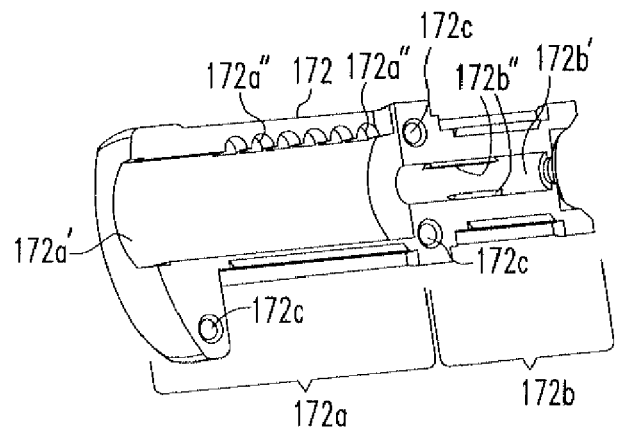
FIG. 16C shows an isometric view of a second part of the hub of FIG. 16A.

FIGS. 16A-16C show a two-part huh 170. The huh 1711 includes a first part 171, as more clearly shown in FIG. 16B, and a second part 172, as more clearly shown in FIG. 16C. Both the first part 171 and the second part 172 include a first section 171a,172a and a second section 171b,172b. The first sections 171a,172a include a depression 171a',172a' and grooves 171a'',172a''. The second sections 171b,172b include a channel 171b',172b' and at least two bosses 171b'',172b'' located within each channel 1711',1721'. The first part 171 also includes pins 171c that, upon coupling of the first part 171 and the second part 172 to form the hub 170, are disposed within holes 172c on the second part 172. Each part 171,172 also includes tabs 171d, 172d located on an outer surface 171b''',172b''' of the second sections 171b, 172b. As shown in FIG. 9C, the second section 171b, 172b is housed within the cannulation 135 of the tubing 130 such that the tabs 171d,172d are disposed within the holes 138 of the tubing 130, thereby coupling the hub 170 to the tubing 130.

Figure 17A:
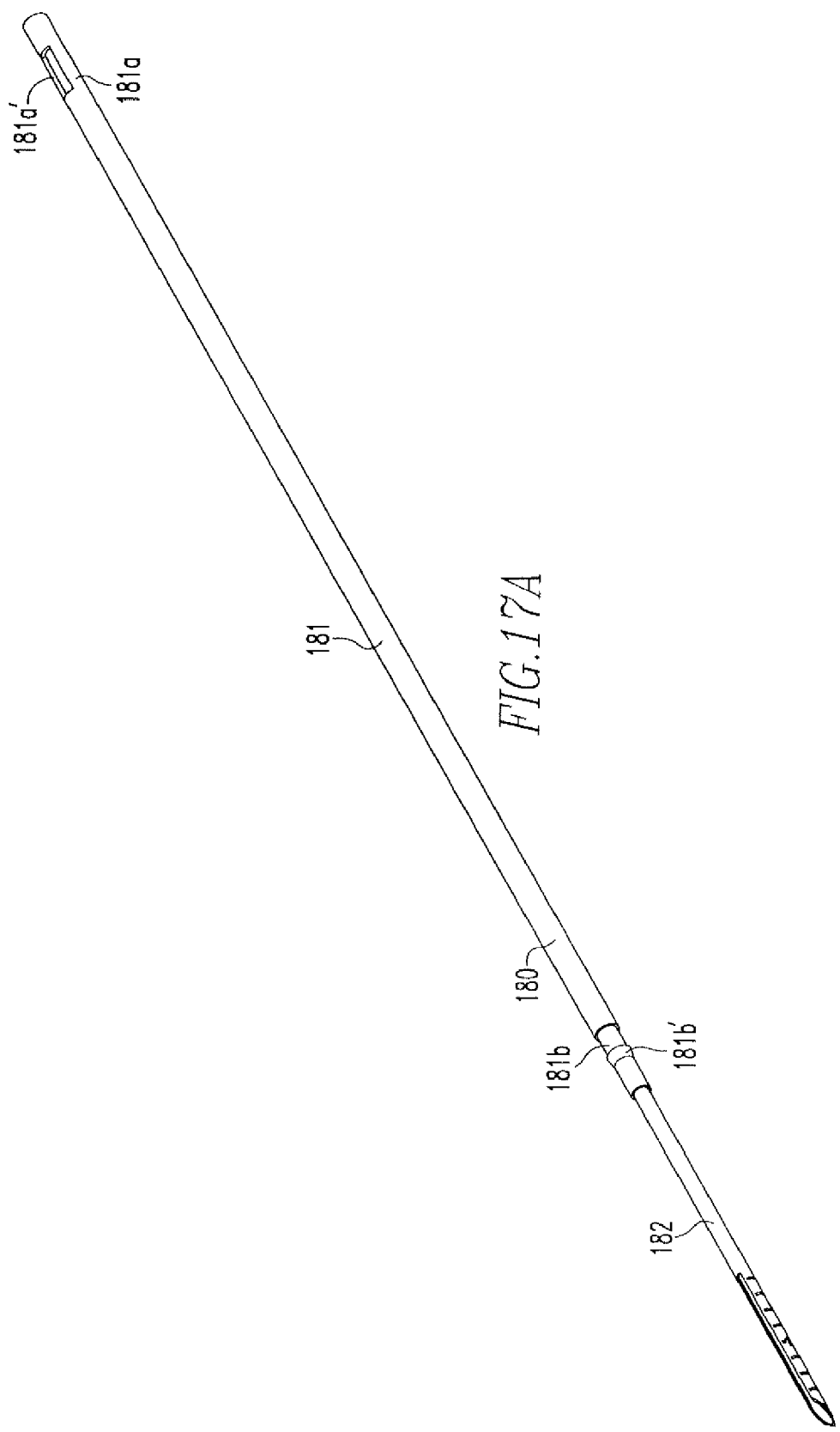
FIG. 17A shows an isometric view of the needle assembly of the tissue repair device of FIGS. 9A-9C.

FIGS. 17A and 17B show a needle assembly 180. The assembly 180 includes a disposal rod 181 and a needle 182 disposed within the rod 181. The rod 181 includes a proximal portion 181a, a distal portion 181b, and an inner channel 181c. The proximal portion 181a includes depressions 181a' on opposite sides of the proximal portion 181a. As shown in FIG. 9C, the needle assembly 180 is disposed within the hub 170, such that the bosses 171b'', 172b'' for both parts 171,172 are disposed within the depressions 181a', thereby coupling the assembly 180 to the hub 170. The distal portion 181b includes a flange 181b'. It is within the scope of this disclosure that the distal portion 181b includes more than one flange 181b'. The needle 182 includes a proximal portion (not shown) housed within the inner channel 181c of the rod 181 and a distal portion 182b including a beveled tip 182b', a slot 182b'' extending from the beveled tip 182b' and including a front portion 182d, a hack portion 182e, and two sides 182f, and laser marks 182b'''. The laser marks 182b''' are used during repair to indicate the depth of the needle 182, as will be further described below.

Figure 18A:
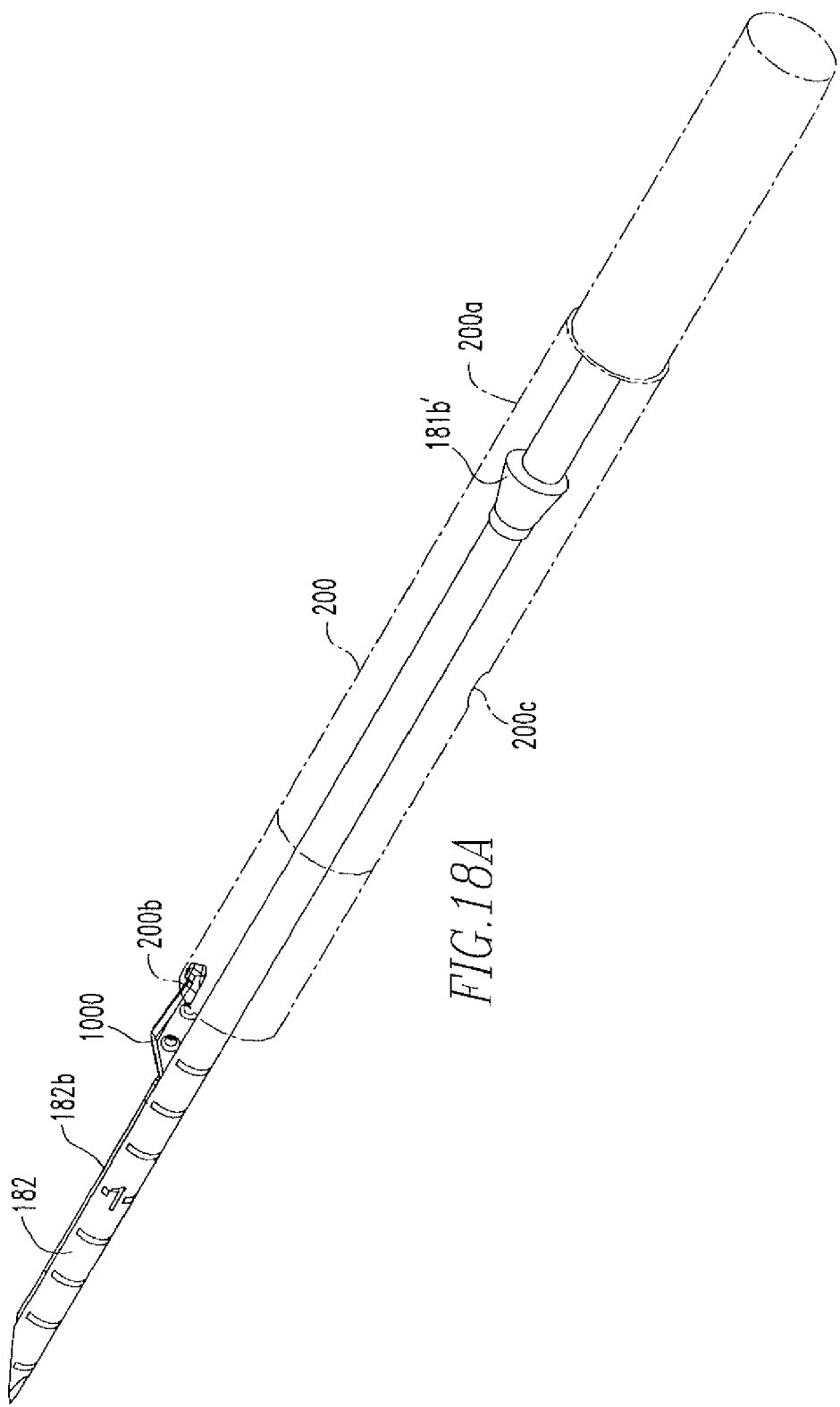
FIGS. 18A-18B show isometric views of the distal end of the needle assembly FIG. 9B with anchors and a transparent tube.
Figure 18B:
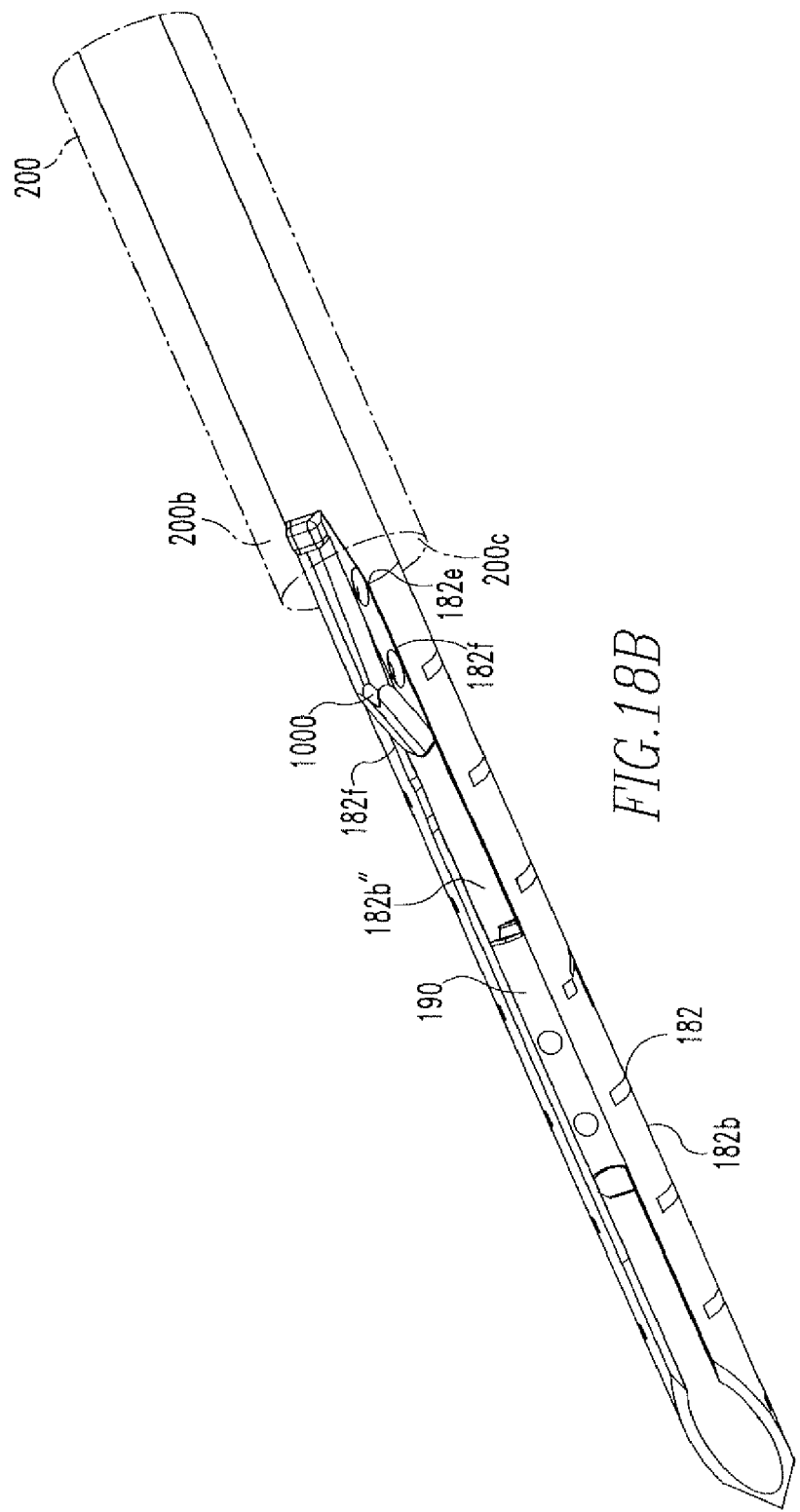
Figure 19:
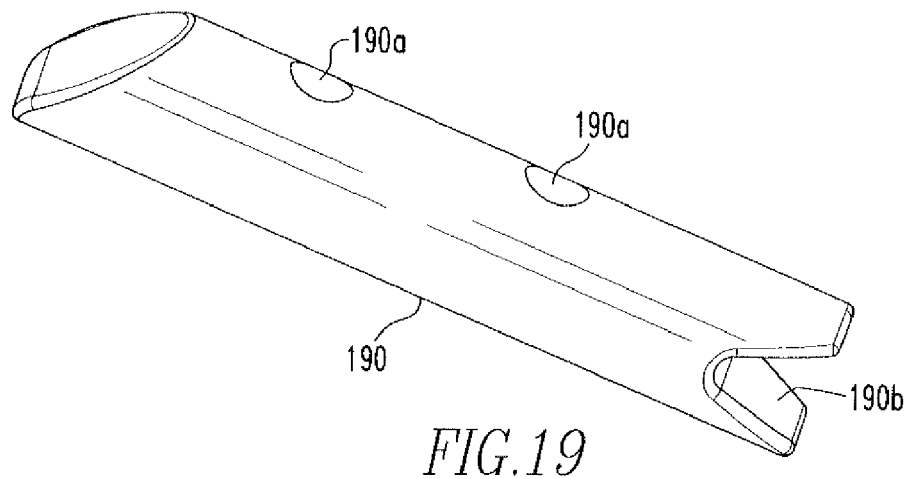
FIG. 19 shows an isometric view of a first anchor of the tissue repair device of 9A-9C.
Figure 20:
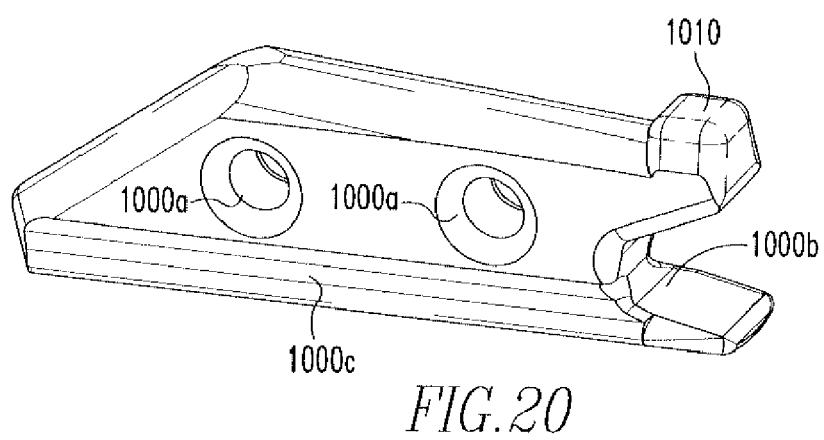
FIG. 20 shows a side view of a second anchor of the tissue repair device of FIGS. 9A-9C.

As shown, in FIGS. 18A and 18B, anchors 190,1000, which are more clearly shown in FIGS. 19 and 20, are coupled to the distal portion 182b of the needle 182. Both anchors 190,1000 include holes 190a, 10000a and slots 190b,1000b. The second anchor 1000 includes channels 1000c on opposite, sides of the anchor 1000 and a protrusion 1010. The second anchor 1000 is coupled to the needle 182, such that the sides 182f of the slot 182b'' are housed within the channels 1000c and the back portion 182e of the slot 1820'' is within slot 1000b. Also shown in FIGS. 18A-18B is a cannulated, transparent tube 200. The tube 200 includes a proximal portion 200a, which is disposed over the distal portion 181b of the rod 181 such that the flange 181b' engages an inner wall 200c of the tube 200, and a distal portion 200b is disposed over the protrusion 1010 of the second anchor 1000. The protrusion 1010 allows for an increased amount of interference between the distal portion 200b of the tube 200 and the anchor 1000 when the distal portion 200b is disposed over the protrusion 1010 of the anchor 100. This increased amount of interference, increases the retention of the anchor 1000 to the needle 182.

The actuator 142 is disposed within needle 182 such that the end portion 142b''' of the actuator 142 is located proximal to the first anchor 190 and distal to the second anchor 1000.

Figure 21:
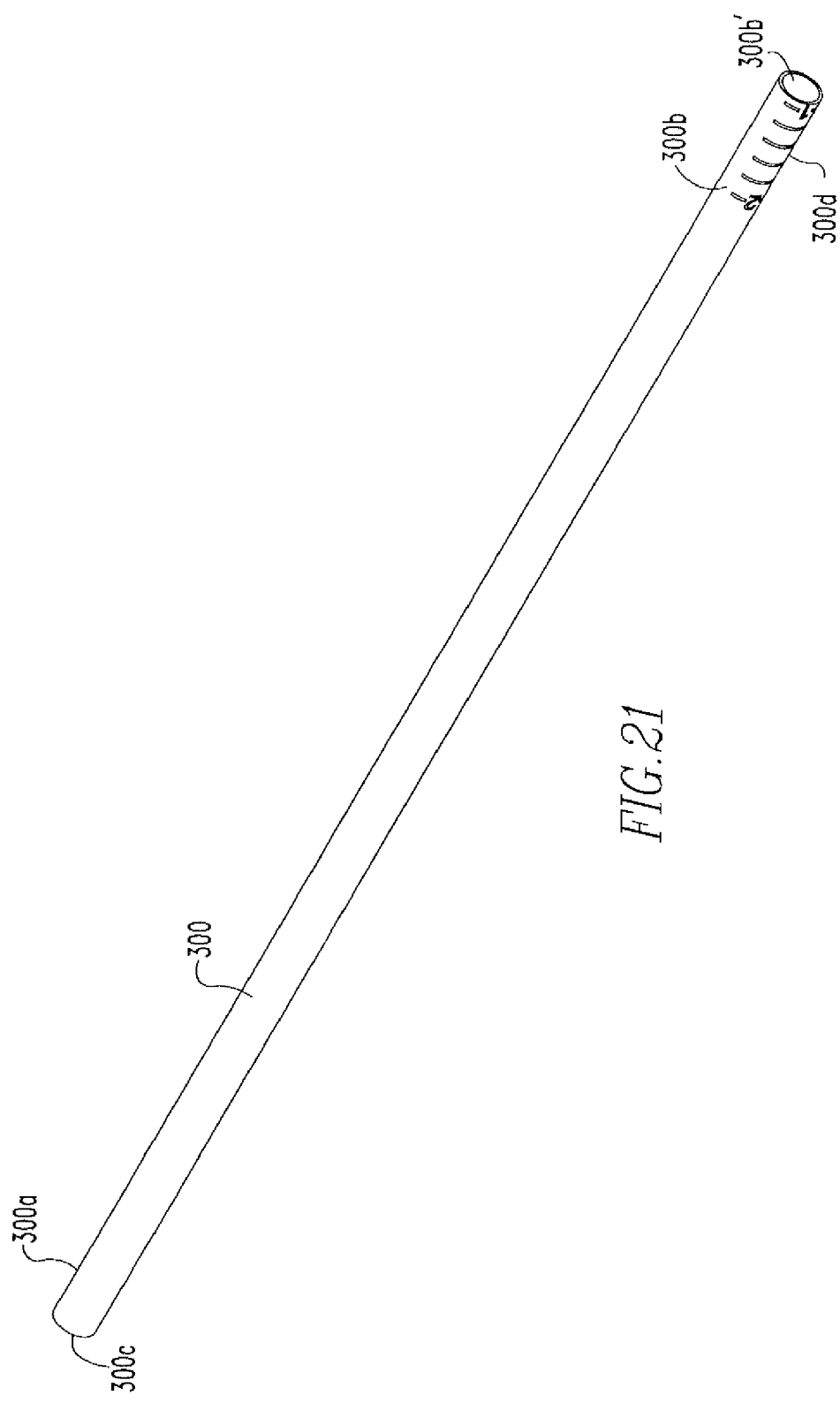
FIG. 21, shows an isometric view of the depth tube of the tissue repair device of FIGS. 9A-9C.
Figure 22A:
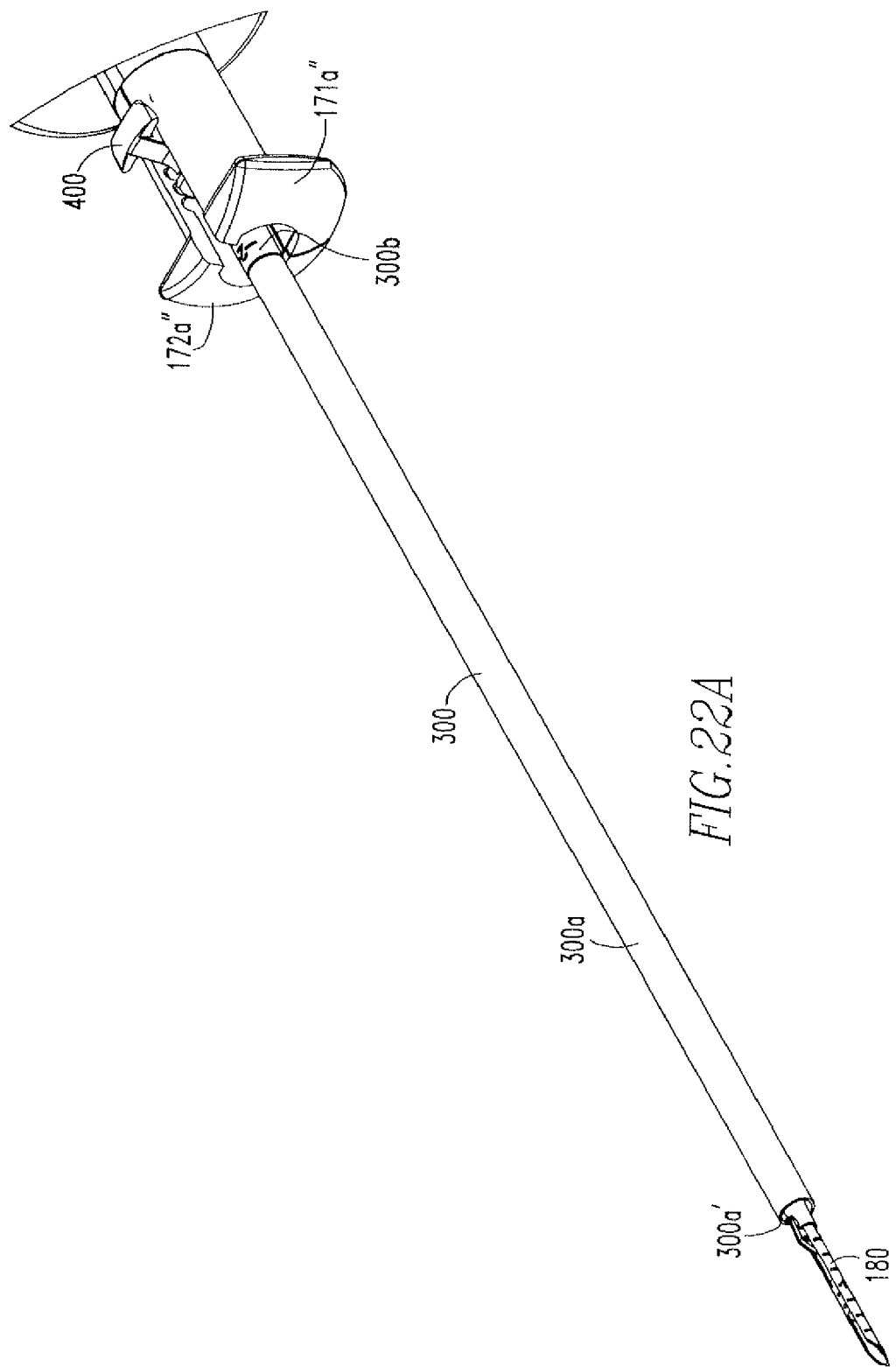
FIG. 22A shows an isometric view of the depth tube of FIG. 21 with the slider coupled to the depth tube and the hub.
Figure 22B:
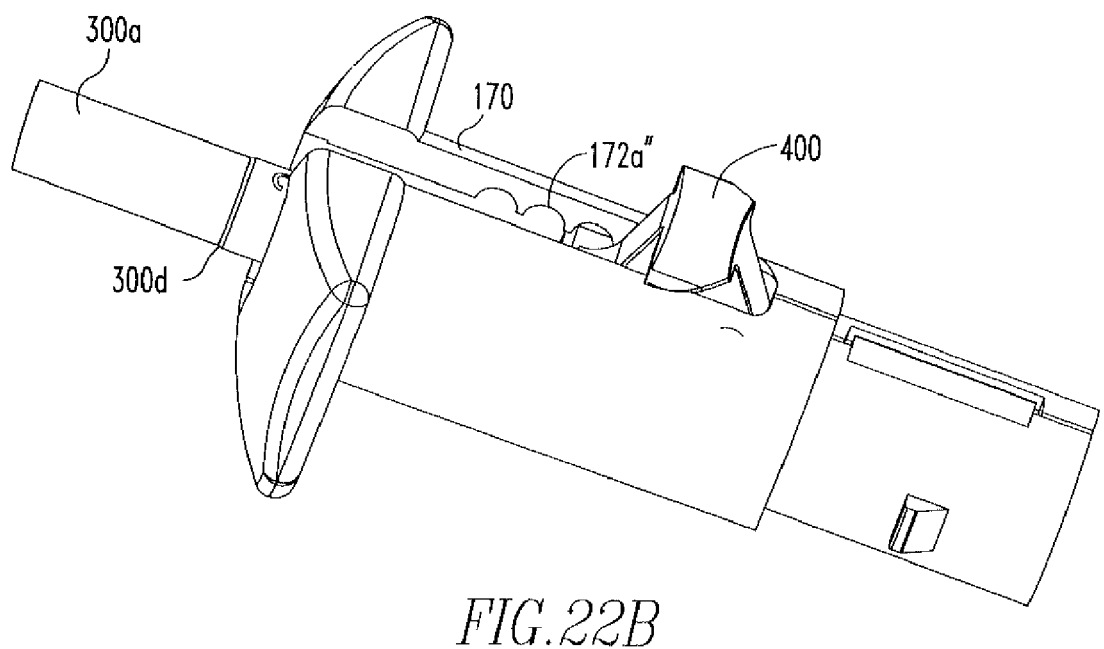
FIG. 22B shows a side view of the slider, depth tube, and hub of FIG. 22A.
Figure 23:
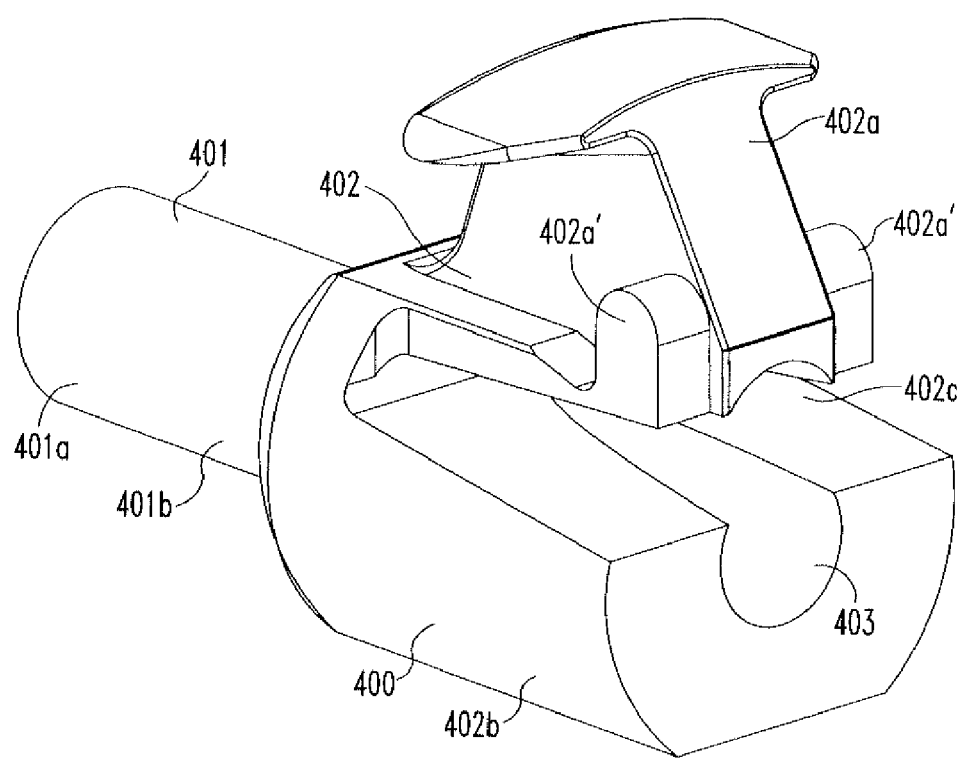
FIG. 23 shows an isometric view of the slider of FIG. 22A.

FIG. 21 shows a depth tube 300, which includes a first portion 300a, a second portion 3001, and a cannulation 390c. As shown in FIGS. 1C and 22A-22B, a slider 400, which is more clearly shown in FIG. 23, is coupled to the depth tube 300 such that a shaft 491 of the slider 400 is housed within the second portion 309b of the depth tube 300. The slider 400 includes the shaft 401, a housing 402 coupled to the shall 401, and a cannulation 403. The shaft 401 includes a distal portion 401a and a proximal portion 401b having a diameter such that the shall 401 engages an inner wall 300b' of the second portion 300b, thereby coupling the slider 400 to the depth tube 300. The housing 402 includes a top portion 402a, a bottom portion 402b, and an opening 402c. The top portion 402a includes tabs 402a'. As shown in FIG. 22B, the housing 402 is located within the hub 170 such that the tabs 402a' are located within the grooves 171a'',172a''. The needle assembly 180 is housed within the cannulation 300c of the depth tube 300. Longitudinal movement of the depth tube 300 occurs via pressing on the top portion 402a of the housing 492 in a direction towards the bottom portion 4020, so as to remove the tabs 402a' from one of the grooves 171a'',172a'', moving the housing 402 longitudinally in a proximal direction towards or away from the handle 110, and then releasing the top portion 402a such that the tabs 402a' are deposited into other one of the grooves 171a'',172a''.

Figure 24A:
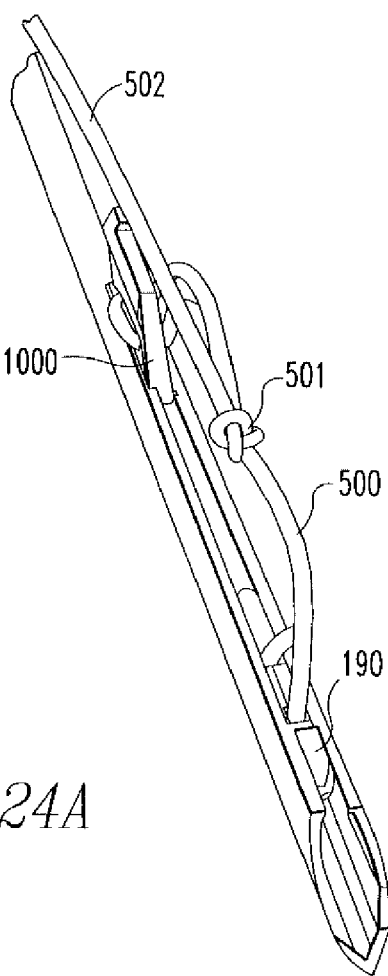
FIG. 24A shows an isometric view of the distal end of the tissue repair device of FIGS. 9A-9C with sutures.

As shown, in FIG. 24A, the anchors 1900,000 are coupled via a flexible member 500, such as a suture, that includes a slip knot 501 located between the anchors 190,1000. The suture 500 is coupled to the anchors 190,1000 and the slip knot 501 is formed via the methods described in the above incorporated US patents and published applications. A free end 502 extends from the slip knot 501 and the suture length between the anchors 190,1900 is reduced upon pulling the free end 502 in one direction, but not in another direction, as will be further described below.

Figure 27:
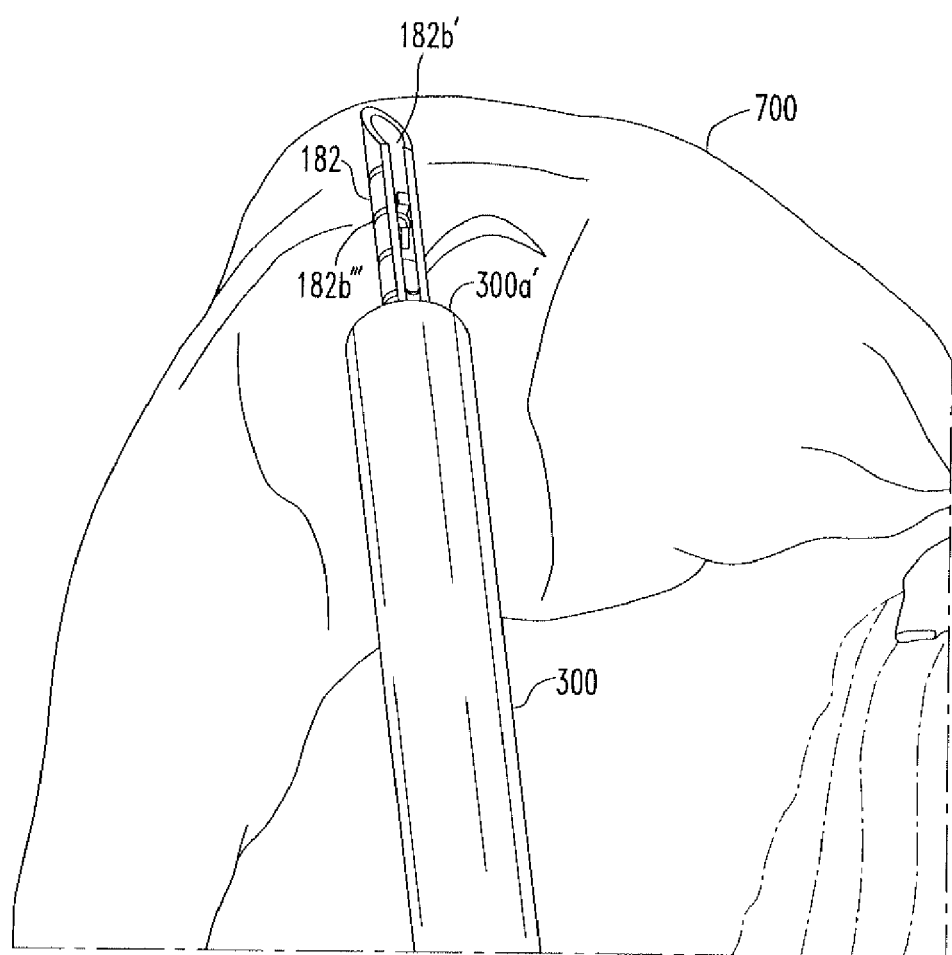
FIGS. 27-30 show a method of tissue repair via use of the tissue repair device of FIGS. 9A-9C.

Referring to FIGS. 27-30, in use, preferably under arthroscopic guidance, the user inserts the device 100 into, for example, the knee joint, until the beveled tip 182b of the needle 182 is in contact with the superior surface of the meniscus 700, as shown in FIG. 27. At this time, the device 100, and especially the starting position of its components, is as shown in FIGS. 24B-24D. Namely, as stated above, the end portion 1421Y''' of the actuator 142 is located proximal to the first anchor 190 and distal to the second anchor 1000 and a distal portion 20015 of the tube 200 is disposed over at least a portion of the second anchor 1000. The first portions 171a, 172a of the hub 170 and specifically the fronts (FIG. 22A, 171a'',172a'') of portions 171a,172a are aligned with the markings 300d of the second portion 300b. Similarly, as can be seen in FIG. 27, the front 300a' of the depth tube 300 is aligned with the markings 182b''' of the needle 182. During repair, as the depth tube 300 is moved longitudinally along the needle 182, the fronts 171a'', 172a'', 300a' of the hub 170 and the depth tube 300 will continue to align with the markings 300d, 182b''' such that the markings 300d, 182b''' that the fronts 171a'', 172a'', 300a' are aligned with will be equivalent to each other. For example, when fronts 171a'', 172a'' are aligned with marking 300d that corresponds to 1 mm, front 300a' is aligned marking 182b''' that corresponds with 1 mm.

Optionally, the depth tube 300 is disposed over the needle assembly 180 and, after insertion of the device 100 into the joint, the tube 300 is moved proximally, in a manner as described above, toward the knob 120 to uncover the distal end 182b of the needle 182, and determine the appropriate needle insertion depth, which the laser marks 182b''', 300d may be used for. In practice, enough of the needle 182 should be exposed to allow for insertion of the needle 182 through the meniscus and subsequent delivery of the anchor 190, but not so much that, the needle 182 will extend into areas behind the meniscus, such as neurovascular areas, where it could cause damage.

In addition to the starting position of the beveled tip 182b' of the needle 182, the starting position of the disk 160 is shown in FIG. 24D. The disk 160 is located such that the protrusions 166 are located in slots 132b, specifically region 132b', and the spikes 163a of the protrusions 166 rest against stepped region 132b'''.

Figure 25:
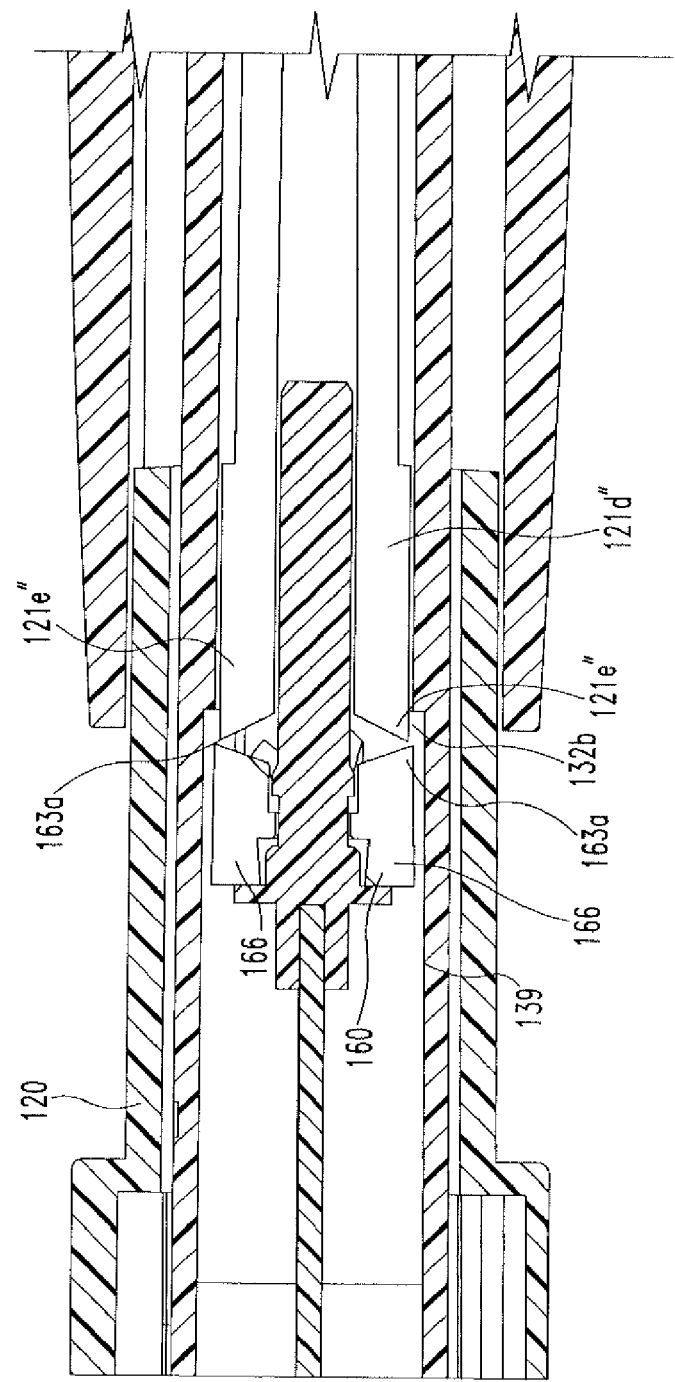
FIG. 25 shows a cross-sectional view of the pusher assembly of the tissue repair device of the present disclosure during deployment of the first anchor.
Figure 26A:
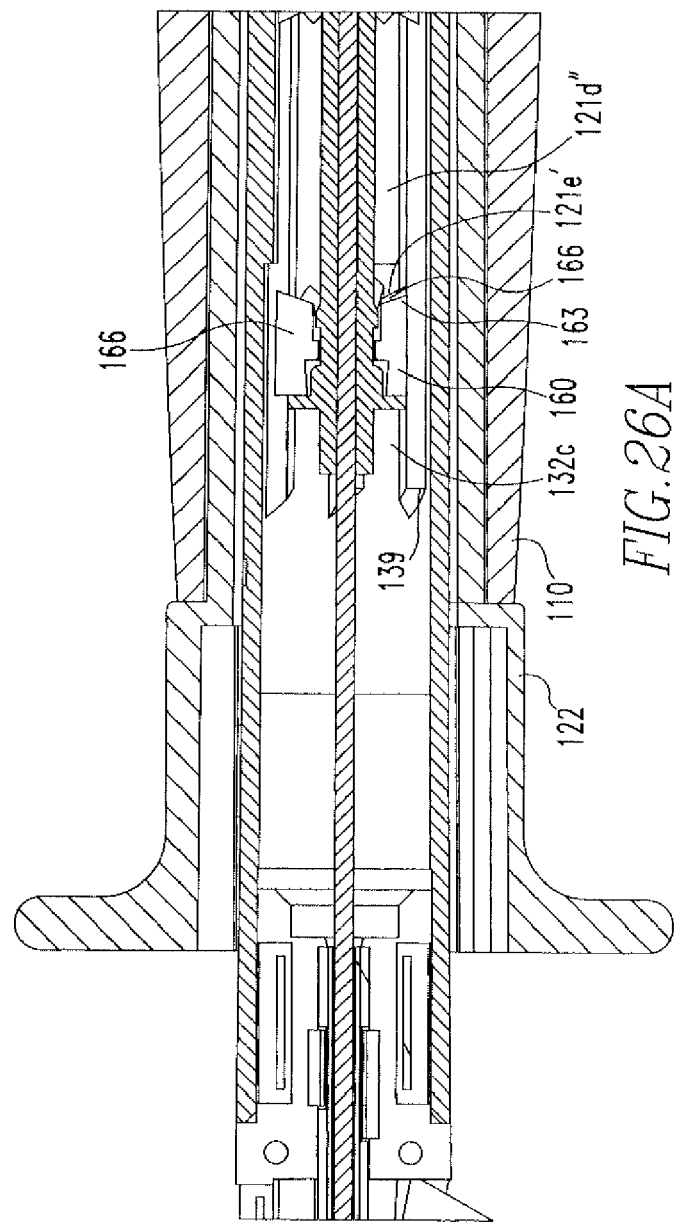
FIG. 26A shows a cross-sectional view of the pusher disk after deployment of the first anchor.
Figure 28:
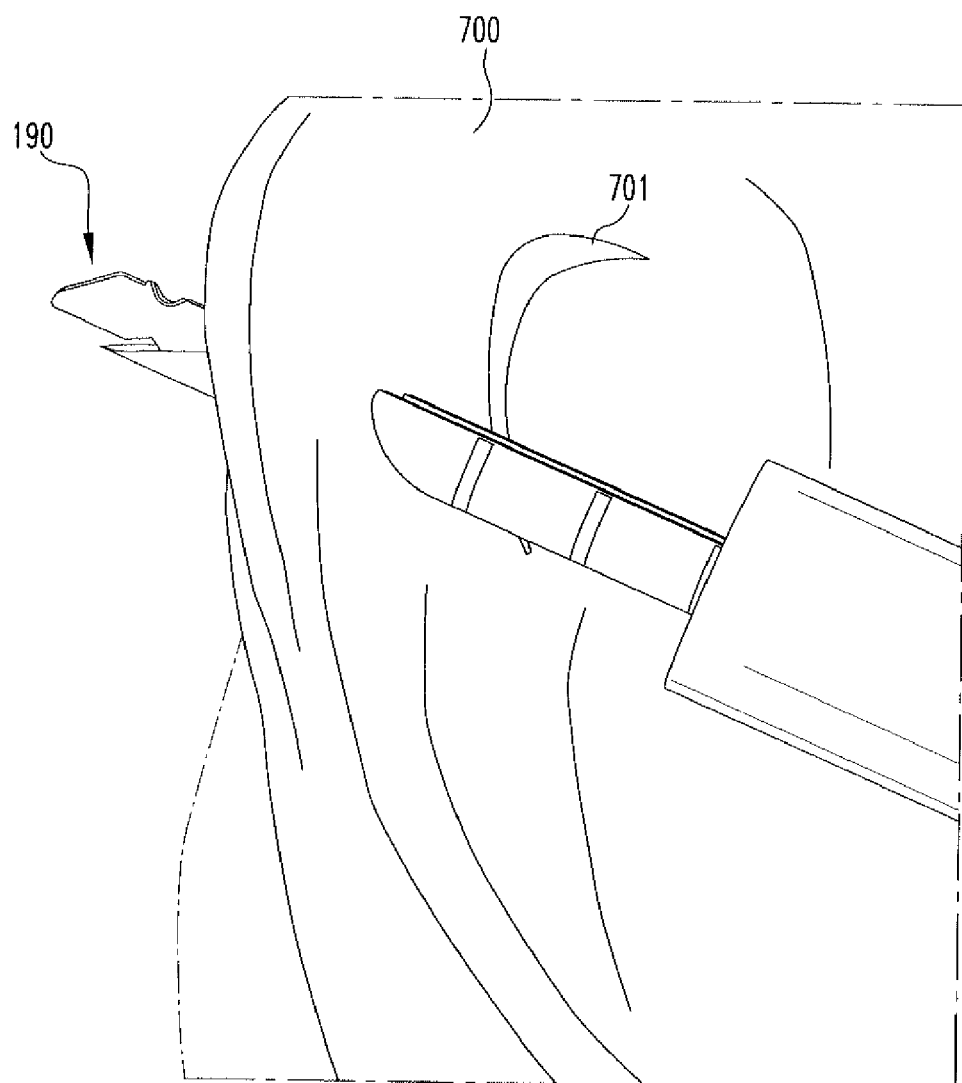

Insertion of the end 182b through the meniscus 700 occurs until the depth tube 300 prevents the needle 182 from being inserted any further or the user decides to discontinue, insertion of the needle 182. The knob 120 is then moved distally over the hub 170 to deploy the First anchor 190, as shown in FIG. 28. At this time, the position of the pusher disk 160 is shown FIG. 25. Specifically, movement of the knob 120 in a distal direction pushes the disk 160 out of slot 1321. In addition, knob movement causes engagement to occur between spikes 163a of disk 160 and spikes 121e'' of rod 121d'', thereby causing the disk 160 to partially rotate. After deployment of the first anchor 190, the knob 120 is moved proximally toward the handle 110. Upon movement of the knob 120 in a proximal direction, the protrusions 166 of the knob 120 engage the rails 139, which cause another partial rotation of the disk 160, thereby locating the protrusions 166 in slots 132c. Once the protrusions 166 are located in slots 132c, the disk 160 continues to move in the proximal direction until the head 122 of the knob 120 rests against the handle 110, as shown in FIG. 26A. FIG. 26A also shows the back portion 163 of the disk 160 resting against the face 121e' of the rod 121d'''. As shown in FIG. 26B, when the disk 160 is positioned as shown in FIG. 26A, the end portion 146b''' of the actuator 142 is located proximal to the second anchor 1000.

Figure 29:
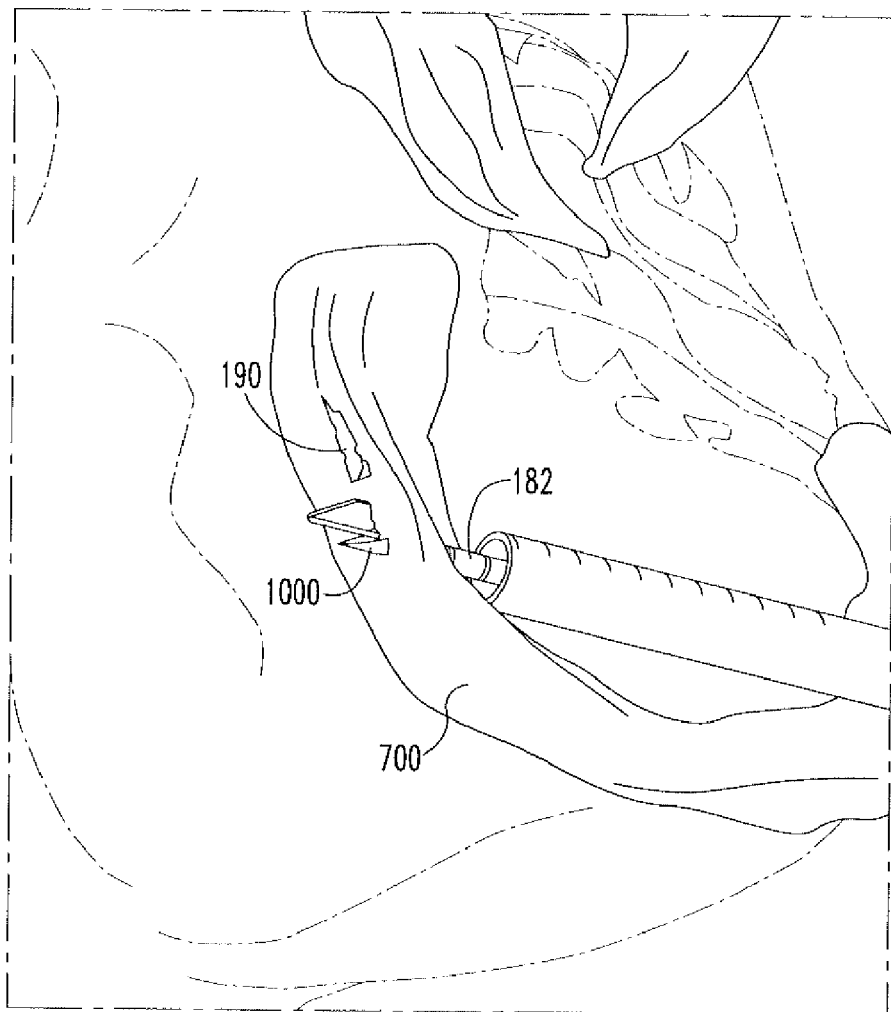

Once the first anchor 190 has been deployed, the needle 132 is removed from the meniscus 700 and re-inserted across the tear 701, as shown in FIG. 29. The knob 120 is, once again, moved distally over the hub 170 to deploy the second anchor 1000. Specifically, when the end portion 142b''' of the actuator 142 is located proximal to the second anchor 1000, the end portion 142b''' is flipped upward, as shown in FIG. 2613, which allows the end portion 142b''' to engage the anchor 1000 and be inserted into the slot 1000b upon movement of the knob 120 in a distal direction. Further movement of the actuator 142 pushes the anchor 1000 out of the needle 182. In addition, knob movement in a distal direction causes the disk 160 to be dispelled from the slot 132b, thereby causing the disk 160 to partially rotate. After deployment of the second anchor 1000, the knob 120 is moved proximally toward the handle 110. Upon movement of the knob 120 in a proximal direction, the protrusions 166 of the disk 160 engage the rails 139, which cause another partial rotation of the disk 160, thereby locating the protrusions 166 in slots 132b. Once the protrusions 166 are located in slots 132b, the disk 160 continues to move in the proximal direction until the spikes 163a of the protrusions 166, once again, rest against stepped region 132b''', as Shown in FIG. 24D.

Figure 30:
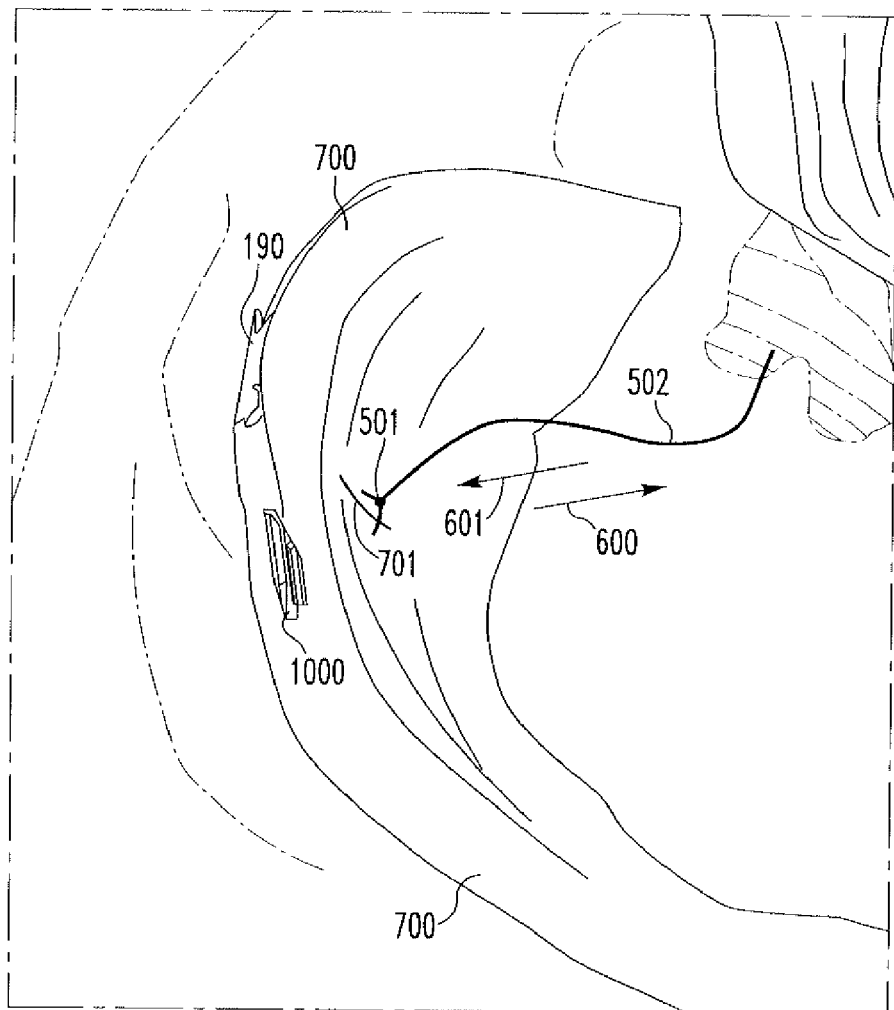

The device 10 is subsequently removed from the knee joint and the free end 502 is pulled in the direction of arrow 600. This shortens the length of suture between anchors 190,1000, bringing sides of tear 701 into juxtaposition, as shown in FIG. 30. Depending on the length of suture between anchors 190,1009, the slip knot 501 will either be on the tissue surface or move within the tissue 700. Slip knot 501 allows the suture 500 to slide in the direction of arrow 601, but does not allow the suture 500 to slide in the opposite direction 600. The tension placed on suture 500 by pulling on the suture 500 relative to anchors 190,1900 acts to turn the anchors 190,1000 such that their long sides are in contact with tissue surface. Excess suture 500 can then be cut off. Further manipulation of suture 509 is not needed to secure anchors 190,1000, although the surgeon may wish to provide additional fastening as a back-up securement measure.

For the purposes of this disclosure, the needle 182, rod 181, actuator 142, and spring 150 are of a biocompatible metal material, such as stainless steel, but may be made from a non-metal material. All of the other components are made from a non-metal material. The anchors 190,1090 and suture 500 are of a polymer material, which may or may not be an absorbable polymer material. The actuator 142 may be coupled to the shaft 141 and the needle 182 may be coupled to the rod 181 via mechanical means, adhesive means, such as a non-toxic, biocompatible, adhesive glue, or other means known to one of skill the art. The device 100 and its components are all made via a method known to one of skill in the art, including, but not limited to injection molding.

As various modifications could be made to the exemplary embodiments, as described above with reference to the corresponding illustrations, without departing from the scope of the disclosure, it is intended that all matter contained in the foregoing description and shown in the accompanying drawings shah be interpreted as illustrative rather than limiting. Thus, the breadth and scope of the present disclosure; should not be limited by any of the above-described exemplary embodiments, but should be defined only in accordance with the following claims appended hereto and their equivalents.

The invention claimed is:

1. A deployment assembly for a tissue repair device, the tissue repair device comprising a needle coupled to a handle, the deployment assembly comprising:
   a knob defining a cannulation, the knob configured to be coupled to a distal end of the handle;
   a tube disposed inside the cannulation of the knob, a distal portion of the tube including first and second slots;
   a pusher assembly at least partially disposed within the tube, the pusher assembly comprising an actuator shaft coupled to a proximal end of an actuator, the actuator shaft operatively coupled to the knob; and
   a rotatable disk disposed about the actuator shaft, an outer surface of the rotatable disk comprising a plurality of protrusions configured to slide within the first and second slots of the tube;
   wherein distal movement of the knob relative to the tube allows for engagement of the actuator with an anchor disposed in the needle to deploy the anchor from the needle.

2. The deployment assembly of claim 1, wherein the knob comprises a head and knob shaft extending proximally from the head, the head comprising a user-manipulatable flange for movement of the knob relative to the tube.

3. The deployment assembly of claim 2, wherein a distal end of the actuator shaft comprises a flanged cap, the rotatable disk being disposed about the shaft in contact with the flanged cap.

4. The deployment assembly of claim 3, further comprising a spring disposed about the actuator shaft such that an end of the spring contacts the flanged cap.

5. The deployment assembly of claim 4, wherein a proximal end of the knob shaft houses a rod, the rod defining an internal cannulation, and wherein a cross-section of a proximal portion of the actuator shaft has a shape configured to couple with a shape of the cannulation of the rod.

6. The deployment assembly of claim 5, wherein:
   a distal face of the rod defines a first plurality of spikes and a first plurality of divots located between the first plurality of spikes, and wherein a proximal face of the rotatable disk defines a second plurality of spikes and a second plurality of divots located between the second plurality of spikes; and
   wherein the spring is configured to bias the proximal face of the rotatable disk against the distal face of the rod, such that the first plurality of spikes and divots engage the second plurality of spikes and divots when the proximal portion of the actuator shaft is coupled to the cannulation of the rod.

7. The deployment assembly of claim 1, wherein a distal portion of the actuator includes a flat top portion and a beveled end portion, the flat top portion and the beveled end portion configured to engage the anchor.

8. The deployment assembly of claim 1, further comprising a hub coupled to a distal end of the tube, the hub configured to engage a depth tube disposed over the needle.

9. The deployment assembly of claim 8, wherein the knob is configured to move distally over the hub to deploy the anchor from the needle.

10. The deployment assembly of claim 1, wherein the tubing is configured to be coupled to the handle.

11. The deployment assembly of claim 1, wherein the first and second slots define rails between the first and second slots, the first and second slots extending an entire length of the rails.

12. The deployment assembly of claim 1, wherein the first slot includes two regions, each of the two regions having different depths, such that a stepped region is formed along the first slot.

13. A method of actuating a deployment assembly of a tissue repair device, the tissue repair device comprising a needle coupled to a handle, the method comprising:
   moving a knob of the deployment assembly distally relative to a tube from a first starting position to a first deployment position, the deployment assembly further comprising:
   the knob defining a cannulation, the knob configured to be coupled to a distal end of the handle;
   the tube disposed inside the cannulation of the knob, a distal portion of the tube including first and second slots, the first and second slots defining rails between the first and second slots;
   a pusher assembly at least partially disposed within the tube, the pusher assembly comprising an actuator shaft coupled to a proximal end of an actuator, the actuator operatively coupled to the knob; and
   a rotatable disk disposed about the actuator shaft, an outer surface of the rotatable disk comprising a plurality of protrusions configured to slide within the first and second slots of the tube;
   wherein the distal movement of the knob relative to the tube allows for engagement of the actuator with a first anchor disposed in the needle to deploy the first anchor from the needle.

14. The method of claim 13, wherein a proximal face of the rotatable disk defines a plurality of spikes and a plurality of divots located between the plurality of spikes.

15. The method of claim 13, wherein the first slot includes two regions, each of the two regions having different depths, such that a stepped region is formed along the first slot.

16. The method of claim 15, wherein, in the first starting position, at least one of the plurality of protrusions of the rotatable disk is located in the first slot such that one of the plurality of spikes rests against the stepped region.

17. The method of claim 16, wherein the distal movement of the knob to the first deployment position pushes the at least one of the plurality of protrusions out of the first slot and causes a first partial rotation of the rotatable disk relative to the tube.

18. The method of claim 17, further comprising moving the knob proximally to a second starting position, the proximal movement causing the plurality of protrusions to engage the rails, further causing a second partial rotation of the rotatable disk, thereby locating at least one of the plurality of protrusions in the second slot.

19. The method of claim 18, further comprising moving the knob distally to a second deployment position, the distal movement causing the rotatable disk to be dispelled from the second slot, further causing a third partial rotation of the rotatable disk, the distal movement of the knob relative to the tube allowing for engagement of the actuator with a second anchor disposed in the needle to deploy the second anchor from the needle.

20. The method of claim 19, further comprising moving the knob proximally to a rest position, the proximal movement causing the plurality of protrusions to engage the rails, further causing a fourth partial rotation of the rotatable risk, thereby locating at least one of the plurality of protrusions in the first slot.

\* \* \* \* \*